US012723098B2

(12) United States Patent
Li et al.

(10) Patent No.: US 12,723,098 B2
(45) Date of Patent: Sep. 1, 2026

(54) ANTI-CLAUDIN 18.2 ANTIBODY AND USE THEREOF

(71) Applicant: CRAGE MEDICAL CO., LIMITED, Hong Kong (CN)

(72) Inventors: Zonghai Li, Xuhui District Shanghai (CN); Peng Wang, Xuhui District Shanghai (CN); Zhen Liu, Xuhui District Shanghai (CN); Huamao Wang, Xuhui District Shanghai (CN)

(73) Assignee: CRAGE MEDICAL CO., LIMITED, Hong Kong (CN)

( * ) Notice: Subject to any disclaimer, the term of this patent is extended or adjusted under 35 U.S.C. 154(b) by 1093 days.

(21) Appl. No.: 17/790,657

(22) PCT Filed: Jan. 4, 2021

(86) PCT No.: PCT/CN2021/070139

§ 371 (c)(1),
(2) Date: Jul. 1, 2022

(87) PCT Pub. No.: WO2021/136550

PCT Pub. Date: Jul. 8, 2021

(65) Prior Publication Data

US 2023/0061005 A1 Mar. 2, 2023

(30) Foreign Application Priority Data

Jan. 3, 2020 (CN) ......................... 202010006872.4

(51) Int. Cl.

| | |
|---|---|
| ***C07K 16/30*** | (2006.01) |
| ***G01N 33/563*** | (2006.01) |
| ***G01N 33/574*** | (2006.01) |
| ***G01N 33/575*** | (2026.01) |

(52) U.S. Cl.

CPC .......... *C07K 16/30* (2013.01); *G01N 33/563* (2013.01); *G01N 33/5758* (2026.01); *C07K 2317/24* (2013.01); *C07K 2317/54* (2013.01); *C07K 2317/55* (2013.01); *C07K 2317/56* (2013.01); *C07K 2317/622* (2013.01)

(58) Field of Classification Search

CPC .... C07K 16/28; C07K 16/30; C07K 16/3046; C07K 2317/24; C07K 2317/33; C07K 2317/34; C07K 2317/54; C07K 2317/55; C07K 2317/56; C07K 2317/622; G01N 33/563; G01N 33/575; G01N 33/5758; G01N 33/577; G01N 33/58; G01N 2333/705

See application file for complete search history.

(56) References Cited

U.S. PATENT DOCUMENTS

| | | | | |
|---|---|---|---|---|
| 9,512,232 B2 | 12/2016 | Sahin et al. | | |
| 10,421,817 B1 | 9/2019 | Hu et al. | | |
| 2015/0147763 A1* | 5/2015 | Sahin | .................. | C07K 16/303 530/387.9 |
| 2019/0233511 A1 | 8/2019 | Wang et al. | | |

FOREIGN PATENT DOCUMENTS

| | | |
|---|---|---|
| CN | 103694353 | 4/2014 |
| CN | 104321345 | 1/2015 |
| CN | 108047331 | 5/2018 |
| CN | 109762067 | 5/2019 |
| CN | 109790222 | 5/2019 |
| CN | 110606891 | 12/2019 |
| EP | 1 997 832 | 12/2008 |
| EP | 3 483 182 | 5/2019 |
| EP | 2 847 225 | 11/2019 |
| EP | 3 666 796 | 6/2020 |
| EP | 3 683 239 | 7/2020 |
| JP | 2015-517476 | 6/2015 |
| JP | 2019-531084 | 10/2019 |
| KR | 10-2015-0008095 | 1/2015 |
| WO | 2013/167153 | 11/2013 |
| WO | 2013/167259 | 11/2013 |
| WO | 2018/006882 | 1/2018 |
| WO | 2019/173420 | 9/2019 |
| WO | 2019/219089 | 11/2019 |

OTHER PUBLICATIONS

Padlan, X-Ray Crystallography of Antibodies, Advances in Protein Chemistry, 49:57-133. (Year: 1996).*
Berglund et al., The epitope space of the human proteome, Protein Science, 17:606-613. (Year: 2008).*
Paul, Fundamental Immunology, 3rd Edition, pp. 292-295. (Year: 1993).*
Rudikoff et al., Proc. Natl. Acad. Sci. USA, 79(6):1979-1983. (Year: 1982).*
Murphy et al., Journal of Immunological Methods, vol. 463, p. 127-133. (Year: 2018).*
Extended European Search Report issued Feb. 2, 2024 in corresponding European Patent Application No. 21736163.3.
Stefan Woll et al., "Claudin 18.2 is a target for IMAB362 antibody in pancreatic neoplasms", International Journal of Cancer, vol. 134, pp. 731-739, 2014.
International Search Report issued Apr. 8, 2021 in International (PCT) Application No. PCT/CN2021/070139, 6 pages.
Singh et al., "Anti-claudin 18.2 antibody as new targeted therapy for advanced gastric cancer", Journal of Hematology & Oncology, 2017, vol. 10, No. 105, pp. 2-6E, 5 pages.

* cited by examiner

*Primary Examiner* — Hong Sang

(74) *Attorney, Agent, or Firm* — Wenderoth, Lind & Ponack, L.L.P.

(57) ABSTRACT

Provided is an antibody or antigen binding fragment, capable of recognizing an antigen peptide comprising SEQ ID NO: 7 (KNKKIYDGG); or recognizing an epitope comprising SEQ ID NO: 7 in Claudin 18.2; preferably recognizing a peptide comprising SEQ ID NO: 6 (KNKKIYDGGART); or recognizing an epitope comprising the SEQ ID NO: 6 in the Claudin 18.2.

13 Claims, 3 Drawing Sheets

Specification includes a Sequence Listing.

```
SP|P56856|CLD18_HUMAN   MSTTTCQVVAFLLSILGLAGCIAATGMDMWSTQDLYDNPVTSVFQYEGLWRSCVRQSSGF 60
SP|P56856-2|CLD18_HUMAN MAVTACQGLGFVVSLIGIAGIIAATCMDQWSTQDLYNNPVTAVFNYQGLWRSCVRESSGF 60
                        *:.*:** :.*::*::*:** **** ** *******:****:**:*:********:****

SP|P56856|CLD18_HUMAN   TECRPYFTILGLPAMLQAVRALMIVGIVLGAIGLLVSIFALKCIRIGSMEDSAKANMTLT 120
SP|P56856-2|CLD18_HUMAN TECRGYFTLLGLPAMLQAVRALMIVGIVLGAIGLLVSIFALKCIRIGSMEDSAKANMTLT 120
                        **** ***:***************************************************

SP|P56856|CLD18_HUMAN   SGIMFIVSGLCAIAGVSVFANMLVTNFWMSTANMYTGMGGMVQTVQTRYTFGAALFVGWV 180
SP|P56856-2|CLD18_HUMAN SGIMFIVSGLCAIAGVSVFANMLVTNFWMSTANMYTGMGGMVQTVQTRYTFGAALFVGWV 180
                        ************************************************************

SP|P56856|CLD18_HUMAN   AGGLTLIGGVMMCIACRGLAPEETNYKAVSYHASGHSVAYKPGGFKASTGFGSNTKNKKI 240
SP|P56856-2|CLD18_HUMAN AGGLTLIGGVMMCIACRGLAPEETNYKAVSYHASGHSVAYKPGGFKASTGFGSNTKNKKI 240
                        ************************************************************

SP|P56856|CLD18_HUMAN   YDGGARTEDEVQSYPSKHDYV 261 SEQ ID NO. 1
SP|P56856-2|CLD18_HUMAN YDGGARTEDEVQSYPSKHDYV 261 SEQ ID NO. 2
                        *********************
```

Figure 1

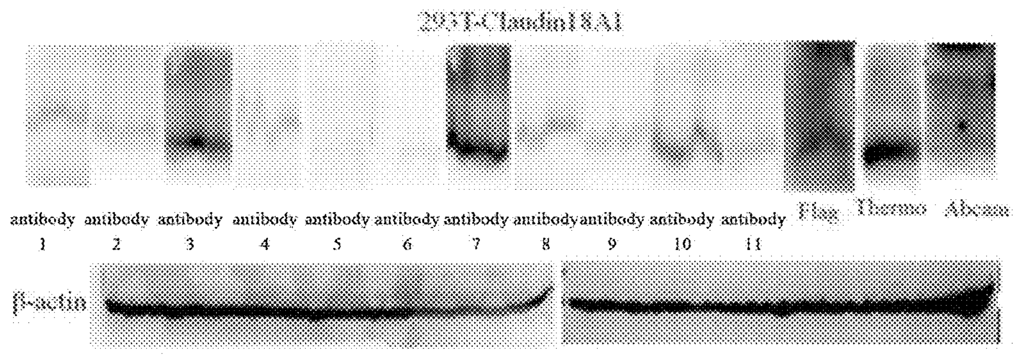

Figure 2A

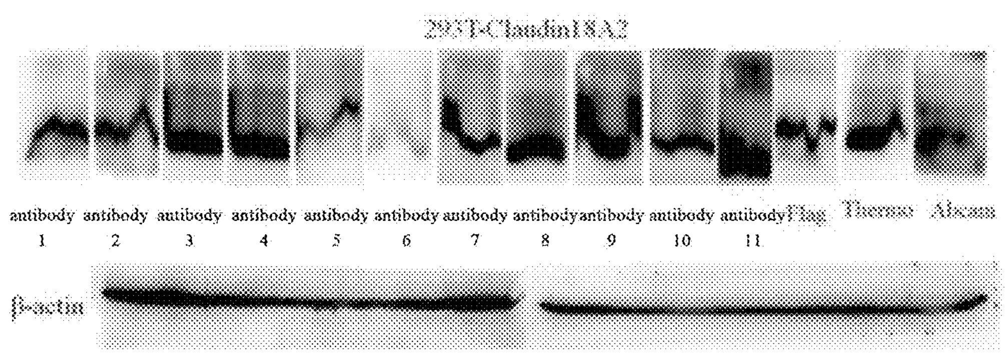

Figure 2B

SEQUENCE LISTING

```
<160> NUMBER OF SEQ ID NOS: 10

<210> SEQ ID NO 1
<211> LENGTH: 261
<212> TYPE: PRT
<213> ORGANISM: Artificial sequence
<220> FEATURE:
<223> OTHER INFORMATION: Claudin 18.1

<400> SEQUENCE: 1
```

```
Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 2
<211> LENGTH: 261
<212> TYPE: PRT
<213> ORGANISM: Artificial sequence
<220> FEATURE:
<223> OTHER INFORMATION: Claudin 18.2

<400> SEQUENCE: 2

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95
```

```
Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 3
<211> LENGTH: 71
<212> TYPE: PRT
<213> ORGANISM: Artificial sequence
<220> FEATURE:
<223> OTHER INFORMATION: Claudin18.2 C terminus

<400> SEQUENCE: 3

Met Met Cys Ile Ala Cys Arg Gly Leu Ala Pro Glu Glu Thr Asn Tyr
1               5                   10                  15

Lys Ala Val Ser Tyr His Ala Ser Gly His Ser Val Ala Tyr Lys Pro
            20                  25                  30

Gly Gly Phe Lys Ala Ser Thr Gly Phe Gly Ser Asn Thr Lys Asn Lys
        35                  40                  45

Lys Ile Tyr Asp Gly Gly Ala Arg Thr Glu Asp Glu Val Gln Ser Tyr
    50                  55                  60

Pro Ser Lys His Asp Tyr Val
65                  70


<210> SEQ ID NO 4
<211> LENGTH: 113
<212> TYPE: PRT
<213> ORGANISM: Artificial sequence
<220> FEATURE:
<223> OTHER INFORMATION: 43-14A2 light chain variable region

<400> SEQUENCE: 4

Asp Ile Val Met Thr Gln Ala Ala Phe Ser Ile Pro Val Thr Leu Gly
1               5                   10                  15

Thr Ser Ala Ser Ile Ser Cys Arg Ser Ser Lys Asn Leu Leu His Ser
            20                  25                  30

Asp Gly Ile Thr Tyr Leu Tyr Trp Tyr Leu Gln Arg Pro Gly Gln Ser
        35                  40                  45

Pro Gln Leu Leu Ile Tyr Arg Val Ser Asn Leu Ala Ser Gly Val Pro
```

-continued

```
    50                  55                  60

Asn Arg Phe Ser Gly Ser Glu Ser Gly Thr Asp Phe Thr Leu Arg Ile
65                  70                  75                  80

Ser Arg Val Glu Ala Glu Asp Val Gly Val Tyr Tyr Cys Val Gln Val
                85                  90                  95

Leu Glu Leu Pro Phe Thr Phe Gly Gly Gly Thr Lys Leu Glu Ile Lys
            100                 105                 110

Arg


<210> SEQ ID NO 5
<211> LENGTH: 115
<212> TYPE: PRT
<213> ORGANISM: Artificial sequence
<220> FEATURE:
<223> OTHER INFORMATION: 43-14A2 heavy chain variable region

<400> SEQUENCE: 5

Gln Ile Gln Leu Val Gln Ser Gly Pro Glu Leu Lys Lys Phe Gly Glu
1               5                   10                  15

Thr Val Lys Ile Ser Cys Lys Ala Ser Gly Tyr Thr Phe Thr Asp Tyr
            20                  25                  30

Ser Ile His Trp Val Lys Gln Ala Pro Gly Lys Gly Leu Lys Trp Met
        35                  40                  45

Gly Trp Ile Asn Thr Glu Thr Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Thr Gly Phe Asp Tyr Trp Gly Gln Gly Thr Thr Leu Thr
            100                 105                 110

Val Ser Ser
        115


<210> SEQ ID NO 6
<211> LENGTH: 12
<212> TYPE: PRT
<213> ORGANISM: Artificial sequence
<220> FEATURE:
<223> OTHER INFORMATION: Binding peptide fragment of antibody 9(14F8)

<400> SEQUENCE: 6

Lys Asn Lys Lys Ile Tyr Asp Gly Gly Ala Arg Thr
1               5                   10


<210> SEQ ID NO 7
<211> LENGTH: 9
<212> TYPE: PRT
<213> ORGANISM: Artificial sequence
<220> FEATURE:
<223> OTHER INFORMATION: Binding peptide fragment of 9G5

<400> SEQUENCE: 7

Lys Asn Lys Lys Ile Tyr Asp Gly Gly
1               5


<210> SEQ ID NO 8
<211> LENGTH: 15
<212> TYPE: PRT
<213> ORGANISM: Artificial sequence
<220> FEATURE:
```

-continued

```
<223> OTHER INFORMATION: Binding polypeptide of antibody 7(9G5)

<400> SEQUENCE: 8

Gly Phe Gly Ser Asn Thr Lys Asn Lys Lys Ile Tyr Asp Gly Gly
1               5                   10                  15


<210> SEQ ID NO 9
<211> LENGTH: 15
<212> TYPE: PRT
<213> ORGANISM: Artificial sequence
<220> FEATURE:
<223> OTHER INFORMATION: Binding peptide fragment of antibody 7(9G5) and
      antibody 9(14F8)

<400> SEQUENCE: 9

Ser Asn Thr Lys Asn Lys Lys Ile Tyr Asp Gly Gly Ala Arg Thr
1               5                   10                  15


<210> SEQ ID NO 10
<211> LENGTH: 15
<212> TYPE: PRT
<213> ORGANISM: Artificial sequence
<220> FEATURE:
<223> OTHER INFORMATION: Binding peptide fragment of of antibody 7(9G5)
      and antibody 9(14F8)

<400> SEQUENCE: 10

Lys Asn Lys Lys Ile Tyr Asp Gly Gly Ala Arg Thr Glu Asp Glu
1               5                   10                  15
```

ANTI-CLAUDIN 18.2 ANTIBODY AND USE THEREOF

FIELD OF THE INVENTION

The present invention relates to the field of immunology, and more specifically, the invention relates to antibodies against Claudin 18.2 and use thereof.

BACKGROUND OF THE INVENTION

Claudin 18 (CLD18) is an endogenous membrane protein located in the tight junctions of epithelium and endothelium with a molecular weight of approximately 27.9 KD. The Genbank accession numbers are, for splice variant 1 (referred to as CLD18A1, CLD18.1 or Claudin 18.1): NP_057453, NM016369, and for splice variant 2 (known as CLD18A2, CLD18.2 or Claudin 18.2): NM_001002026, NP_001002026. CLD18A1 is selectively expressed in normal lung, whereas CLD18A2 is expressed in normal stomach and the expression is restricted to differentiated short-lived gastric epithelial cells. However, in a variety of tumor cells, CLD18A2 showed strong expression. It has been found that, Claudin18.2 was expressed in gastric cancer, esophageal cancer, pancreatic cancer, lung cancer (e.g., Non-small cell lung cancer (NSCLC)), ovarian cancer, colon cancer, liver cancer, breast cancer, head and neck cancer, and tumors of the biliary system (e.g., gallbladder cancer, bile duct cancer) and their metastatic cancers, and gastric cancer metastases such as Krukenberg tumor, peritoneal metastases and lymph node metastases.

CLDN18 is a four-transmembrane protein with two extracellular segments called loop 1 and loop 2. Human CLDN18A2 (SEQ ID NO:2) is highly homologous to human CLDN18A1 (SEQ ID NO:1) and the results of homology comparison between them are shown in FIG. 1. Only the first transmembrane (TM) region at the N terminus and loop 1 are partially different, while the rest of the amino acid sequence is identical.

SUMMARY OF THE INVENTION

The present invention utilizes the C-terminal polypeptide of CLDN18A2 to immunize mice, and although the peptide is identical in sequence in both splice variants, we obtain multiple antibodies with significant tissue specificity that can be used in the clinical diagnosis of CLDN18A2-positive tumors.

In a first aspect, the present invention provides an antibody or antigen-binding fragment wherein the antibody or antigen-binding fragment is capable of recognizing an antigenic peptide comprising the sequence shown in SEQ ID NO: 7 (KNKKIYDGG); or the antibody or antigen-binding fragment is capable of recognizing an epitope comprising the sequence shown in SEQ ID NO: 7 in Claudin18.2.

In a further preferred embodiment, the antibody or antigen-binding fragment is capable of recognizing a peptide comprising the sequence shown in SEQ ID NO: 6 (KNKKIYDGGART); or the antibody or antigen-binding fragment is capable of recognizing an epitope comprising the sequence shown in SEQ ID NO: 6 in Claudin18.2.

In a further preferred embodiment, the antibody or antigen-binding fragment is capable of recognizing an antigenic peptide comprising the sequence shown in SEQ ID NO: 8 (GFGSNTKNKKIYDGG), 9 (SNTKNKKIYDGGART) or 10 (KNKKIYDGGARTEDE); or the antibody or antigen-binding fragment is capable of recognizing an epitope comprising the sequence shown in SEQ ID NO: 8, 9 or 10 in Claudin18.2.

Preferably, the antibody or antigen-binding fragment is capable of recognizing the antigenic peptide comprising the sequence shown in SEQ ID NO: 9 or 10; or the antibody or antigen-binding fragment is capable of recognizing the epitope comprising the sequence shown in SEQ ID NO: 9 or 10 in Claudin18.2.

In a further preferred embodiment, the antibody is an antibody produced by the hybridoma cell line deposited with the accession number CCTCCNO.C202007 or CCTCCNO.C202008, wherein an antibody produced by the hybridoma cell line CCTCCNO.C202007 is antibody 9 and an antibody produced by the hybridoma cell line CCTCCNO.C202008 is antibody 7.

In further preferred embodiments, the antibody or antigen-binding fragment is a mouse-derived antibody, a chimeric antibody, a humanized antibody, or a fully human antibody.

In further preferred embodiments, the antibody or antigen-binding fragment is a humanized antibody or chimeric antibody of an antibody produced by the hybridoma cell line deposited with accession number CCTCCNO.C202007 (antibody 9) or CCTCCNO.C202008 (antibody 7).

In a further preferred embodiment, the antibody or antigen-binding fragment is a variant of the antibody produced by the hybridoma cell line deposited with accession number CCTCCNO.C202007 or CCTCCNO.C202008; wherein the antibody produced by the hybridoma cell line CCTCCNO.C202007 is antibody 9, and the antibody produced by the hybridoma cell line CCTCCNO.C202008 is antibody 7

Preferably, the variant has at least 80%, 85%, 90%, 91%, 92%, 93%, 94%, 95%, 96%, 97%, 98%, or 99% homology to antibodies produced by the hybridoma cell line deposited with the accession number CCTCCNO.C202007 or CCTCCNO.C202008.

In a further preferred embodiment, the antibody fragment is an antibody fragment of the antibody produced by the hybridoma cell line deposited with the accession number CCTCCNO.C202007 or CCTCCNO.C202008.

Preferably, the antibody fragment is a scFv, a Fab fragment, a Fd fragment, a Fv fragment, a F(ab')2 fragment, or a single domain antibody.

Wherein the antibody produced by the hybridoma cell line CCTCCNO.C202007 is antibody 9 and the antibody produced by the hybridoma cell line CCTCCNO.C202008 is antibody 7.

In a further preferred embodiment, the antibody or antigen-binding fragment binds to a cell expressing Claudin 18.2; preferably, the amino acid sequence of Claudin 18.2 is shown in SEQ ID NO: 2, SEQ ID NO: 2 is:

```
MAVTACQGLGFVVSLIGIAGIIAATCMDQWSTQDLYNNPVTAVFNYQGLW
RSCVRESSGFTECRGYFTLLGLPAMLQAVRALMIVGIVLGAIGLLVSIFA
LKCIRIGSMEDSAKANMTLTSGIMFIVSGLCAIAGVSVFANMLVTNFWMS
TANMYTGMGGMVQTVQTRYTFGAALFVGWVAGGLTLIGGVMMCIACRGLA
PEETNYKAVSYHASGHSVAYKPGGFKASTGFGSNTKNKKIYDGGARTEDE
VQSYPSKHDYV.
```

In a further preferred embodiment, the antibody or antigen-binding fragment specifically binds to gastric tissue.

Preferably, the antibody or antigen-binding fragment specifically binds to the gastric tissue and does not bind to lung tissue.

In a second aspect of the invention, provided is a conjugate, wherein the conjugate comprises the antibody or antigen binding fragment according to any one of claims 1-9, and at least one detectable label.

Preferably, the detectable label is a fluorescent label, a chromogenic label, a luminescent label, a chromophore label, a radioisotope label, an isotope label, an isobaric label, an enzyme label, a particle label, a nucleic acid or a protein detected by using a binding agent.

In a third aspect of the present invention, provided is a hybridoma, which is capable of producing the antibodies of the present invention as described above.

In a further preferred embodiment, the hybridoma has a deposited accession number CCTCCNO.C202007 or CCTCCNO.C202008.

In a fourth aspect of the present invention, provided is a method for detecting the expression of Claudin18.2 in a sample to be tested, wherein the method comprises: contacting the sample to be tested with any of the antibodies or antigen-binding fragments of the present invention as described above, or with any of the conjugates of the present invention as described above; detecting the state of a complex formed by the antibody or antigen-binding fragment, or the conjugate and Claudin18.2.

In a fourth aspect of the present invention, provided is a method for diagnosing, detecting or monitoring cancer, wherein the method comprises:

contacting a sample to be tested with the antibody or antigen-binding fragment of the present invention as described above, or with the conjugate of the present invention as described above; detecting the amount of a complex formed by the antibody or antigen-binding fragment, or the conjugate and Claudin18.2.

In a fourth aspect of the present invention, provided is a method for analyzing whether a tumor can be treated by an oncology therapy targeting Claudin18.2, wherein the method comprises:

(i) contacting a sample comprising a tumor cell with the antibody or antigen binding fragment of the present invention as described above, or with the conjugate of the present invention as described above.

(ii) detecting the amount of a complex formed by the antibody or antigen-binding fragment, or the conjugate and Claudin18.2.

Preferably, the tumor cell is a gastric cancer cell, an esophageal cancer cell, a pancreatic cancer cell, a lung cancer cell, an ovarian cancer cell, a colon cancer cell, a liver cancer cell, a head and neck cancer cell, or a biliary system tumor cell (e.g., a gallbladder cancer cell, a bile duct cancer cell).

More preferably, the tumor cell is a gastric cancer cell, an esophageal cancer cell, a pancreatic cancer cell, or a biliary system tumor cell.

In a fifth aspect of the present invention, provided is an assay kit comprising the antibody or antigen-binding fragment of the present invention as described above or the conjugate of the present invention as described above.

In a further preferred embodiment, wherein the Claudin18.2 comprises the amino acid sequence of SEQ ID NO: 2 in the sequence listing or a variant thereof.

In a sixth aspect of the present invention, provided is a method for producing a monoclonal antibody targeting Claudin18.2, wherein the method comprises employing a polypeptide containing the sequence shown in SEQ ID NO: 6, 7, 8, 9 or 10 as an immunogen or using a polypeptide having at least 80%, 85%, 90%, 91%, 92%, 93%, 94%, 95%, 96%, 97%, 98%, or 99% homology to the sequence shown in SEQ ID NO: 6, 8, 9, or 10 as an immunogen, and after immunization of an animal, a B cell from the in animal is taken and fused with a myeloma cell to obtain a hybridoma cell to produce a monoclonal antibody.

Preferably, the animal is a mouse.

Preferably, the B cell is derived from a spleen cell.

In a further preferred embodiment, further comprising isolating the monoclonal antibody from the hybridoma cell.

In further preferred embodiments, the polypeptide shown in SEQ ID NO: 3 (MMCIACRGLAPEETNYKAVSYHASGHSVAYKPGGFKASTGFGSNTKNKKIY DGGARTEDEVQSYPSKHDYV) is used as the immunogen.

In further preferred embodiments, wherein the monoclonal antibody specifically binds to the antigen.

In further preferred embodiments, further comprising producing a modified form of the monoclonal antibody that retains specific binding to the antigen.

In a further preferred embodiment, wherein the modified form of the monoclonal antibody is a humanized antibody.

All publications, patents and patent applications referred to in this specification are incorporated herein by reference, said references being made to the same extent as if each individual publication, patent or patent application had been specifically and individually directed to be incorporated by reference.

BRIEF DESCRIPTION OF THE DRAWINGS

FIG. 1: Results of sequence homology comparison between Claudin 18.2 and Claudin 18.1.

FIG. 2A: Results of Western Blot identification of binding of antibody to 293T-Claudin18.1 cell lysate.

FIG. 2B: Results of Western Blot identification of binding of antibody to 293T-Claudin18.2 cell lysate.

DETAIL DESCRIPTION OF THE INVENTION

Figure 3:
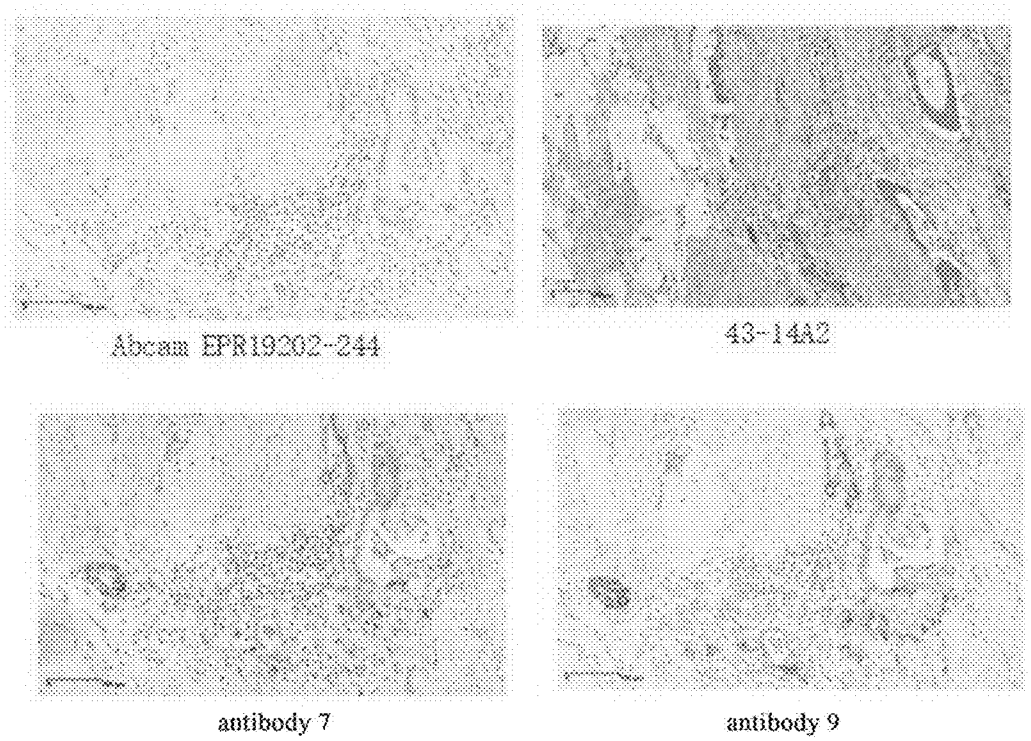
FIG. 3: Results of staining of antibody 7 and antibody 9 on a gastric cancer sample F163060A1.

The following specific description shows in detail the embodiments disclosed herein. It should be understood that this specification is not intended to be limited to the specific embodiments disclosed herein, as changes can occur. It will be understood by those skilled in the art that what is disclosed in this specification can be altered or changed in a variety of ways while all of which are covered within the scope and principles disclosed. Unless otherwise noted, each embodiment may be combined with any other embodiment at will.

Certain embodiments disclosed herein contain numerical ranges, and certain aspects of the invention may be described in terms of ranges. Unless otherwise stated, it should be understood that the numerical ranges or description by way of ranges are for the purpose of brevity and convenience only and should not be considered as strictly limiting the scope of the present invention. Thus, a description by way of a range should be considered to specifically disclose all possible subranges and all possible specific numerical points within that range, as those subranges and numerical points are expressly written out herein. For example, the description of a range from 1 to 6 should be considered to specifically disclose the subranges from 1 to 3, 1 to 4, 1 to 5, 2 to 4, 2 to 6, 3 to 6, etc., and the specific numerical points within those ranges, such as 1, 2, 3, 4, 5, 6. The above principles apply equally regardless of the width or narrowness of the value ranges described. When a range description is used, the range includes the endpoints of the range.

When referring to measurable values such as quantities, temporary durations, etc., the term "approximately" means a variation that includes±20%, or in some cases±10%, or in some cases±5%, or in some cases #1%, or in some cases±0.1% of the specified value.

The term "antibody" is used herein to include both intact antibodies and antigen-binding fragments. Naturally occurring "antibodies" are glycoproteins containing at least two heavy (H) chains and two light (L) chains linked by disulfide bonds between the chains. Each heavy chain consists of a heavy chain variable region (abbreviated as VH herein) and a heavy chain constant region. The heavy chain constant region consists of 3 domains CH1, CH2 and CH3. Each light chain consists of a light chain variable region (abbreviated as VL herein) and a light chain constant region.

The light chain constant region consists a domain CL. The VH and VL regions can be further subdivided into regions with high variability called complementarity determiningregions (CDRs) spaced by more conservative regions called framework regions (FRs). Each VH and VL consists of three CDRs and four FRs arranged in the following order: FR1, CDR1, FR2, CDR2, FR3, CDR3, FR4 from the amino terminus to the carboxyl terminus. The variable regions of the heavy and light chains contain binding domains that interact with an antigen. The antibodies may be derived from various species including, but not limited to, mouse, rat, rabbit, guinea pig, and human. Antibodies also include chimeric antibodies having an antibody constant region from one species (preferably human) with an antigen binding site from another species. Antibodies also include humanized antibodies having an antigen binding site of an antibody from a non-human species with a constant region and a framework region of human origin. The antibodies described herein may be monoclonal antibodies, i.e., preparations of antibody molecules having a single molecular composition. The system used to prepare hybridomas secreting monoclonal antibodies is preferably a mouse system. Immunological manipulations and techniques for isolating immunized splenocytes for fusion are known in the art. Mouse myeloma cell and mouse splenocyte fusion protocols are also known. Other systems for the preparation of hybridomas secreting monoclonal antibodies are preferably rat and rabbit systems (e.g., as described in Spieker-Polet et al., Proc. Natl. Acad. Sci. U.S.A. 92: 9348 (1995). The antibodies described herein may be recombinant antibodies, i.e., all antibodies prepared, expressed, produced or isolated by recombinant means, such as (a) antibodies isolated from animals whose immunoglobulin genes are transgenic or transchromosomal (e.g., mice) or from hybridomas prepared therefrom, (b) antibodies isolated from host cells transformed to express said antibodies (e.g., transfected tumors), (c) antibodies isolated from recombinant combinatorial antibody libraries, and (d) antibodies prepared, expressed, produced, or isolated by any other means involving splicing of immunoglobulin gene sequences into other DNA sequences. Antibodies may be produced by a variety of techniques, such as the hybridoma technique of Kohler et al., Nature 256: 495 (1975), or other techniques for producing monoclonal antibodies, such as phage display techniques.

Nucleotide sequences from hybridoma heavy- and light-chain transcripts are used to design overlapping sets of synthetic oligonucleotides to product synthetic V sequences with the same amino acid coding capacity as the natural sequences. The synthetic heavy- and K-chain sequences can differ from the natural sequences in three ways: by interrupting the repeated nucleotide base strings to facilitate oligonucleotide synthesis and PCR amplification; by incorporating an optimal translation start site according to Kozak's rule (Kozak, 1991, J. Biol. Chem. 266: 19867-19870); and by a modified HindIII site upstream of the translation initiation site.

For the heavy and light chain variable regions, the optimized sequences of the coding strand and the corresponding non-coding strand are interrupted into 30-50 nucleotides at approximately the midpoint of the corresponding non-coding oligonucleotide. Thus, for each chain, said oligonucleotides can be assembled into overlapping double-stranded sets spanning a region of 150-400 nucleotides. The library is then used as a template to product PCR amplification products of 150-400 nucleotides. A single variable region oligonucleotide group is usually divided into two libraries, which are each amplified to produce two overlapping PCR products. These overlapping products are then combined by PCR amplification to form the complete variable region. Overlapping fragments of the heavy or light chain constant region may also be included in the PCR amplification to produce a fragment of the construct that can be easily cloned into the expression vector. The reconstructed chimeric or humanized heavy and light chain variable regions are then combined with the cloned promoter sequence, leading sequence, translation initiation sequence, constant region sequence, 3' untranslated sequence, polyadenylation sequence and transcription termination sequence to form the expression vector construct. The heavy chain and light chain expression constructs can be combined into a single vector, cotransfected, sequentially transfected or separately transfected into host cells, followed by fusion to form host cells expressing both chains. Construction of plasmids for human IgGκ expression vectors allows PCR-amplified V heavy chain and Vκ light chain cDNA sequences to be used to reconstitute intact heavy and light chain minigenes. These plasmids can be used to express either fully human antibodies or chimeric IgG1κ or IgG4κ antibodies. Similar plasmids can be constructed to express other heavy chain isoforms, or to express antibodies containing A light chains.

The term "antigen-binding fragment" refers to one or more fragments of an antibody that retains specific antigen-binding ability, and covers binding fragments including (i) Fab fragments, monovalent fragments consisting of VL, VH, CL and CH domain; (ii) F(ab')2 fragments, bivalent fragments comprising two Fab fragments linked by disulfide bonds at the hinge region; (iii) Fd fragments consisting of VH and CH domains; (iv) Fv fragments consisting of the VL and VH domains of a single arm of the antibody; (v) single-domain antibody fragments consisting of a VH domain; (vi) isolated complementarity determining regions (CDRs), and (vii) combinations of two or more isolated CDRs optionally linked by synthetic linkers. It also includes single-chain antibodies (or single-chain Fv (scFv)) formed by using a recombinant method to link the two domains VL and VH of an FV segment by a synthetic linker.

The binding of the antibody or antigen-binding fragment of the present invention to the target antigen Claudin18.2 can be characterized or expressed by any method known in the art, for example, the binding can be characterized by binding affinity. Binding affinity can be determined by any method known in the art, such as ELISA, Western blotting, immunofluorescence, and flow cytometry analysis. Flow cytometry can demonstrate the presence of antibodies in the serum of immunized mice or demonstrate that monoclonal antibodies bind to live cells. Cell lines naturally expressing or expressing antigen after transfection and negative controls lacking antigen expression (grown under standard growth conditions) are mixed with multiple concentrations of monoclonal antibodies in hybridoma supernatant or in PBS containing 1% FBS and incubated at 4° C. for 30 minutes. After washing, APC- or Alexa647-labeled anti-IgG antibodies were conjugated to the monoclonal antibodies that bound the antigen under the same conditions as the primary antibody staining. Samples are analyzed with a FACS instrument in which gate is set for individual live cells using light scattering and side scattering properties. The use of cotransfection allows differentiation of antigen-specific monoclonal antibodies from non-specific binders in individual measurements. Cells transiently transfected with plasmids encoding antigens and fluorescent labels are stained as described above. Transfected cells can be detected in a different fluorescent channel than antibody-stained cells. Since most transfected cells express both transgenes, the antigen-specific monoclonal antibody binds preferentially to cells expressing the fluorescent label, and the non-specific antibody binds to untransfected cells in a comparable ratio. Cells can be stained exactly as described above, or they can be examined by fluorescence microscopy.

When measured in an in vitro binding assay using cells expressing Claudin 18.2, the binding affinity of the antigen-binding moiety disclosed herein can be determined. The binding affinity of the antigen-binding moiety of the test can be expressed as Kd, which is the equilibrium dissociation constant between the antibody and its respective antigen.

In some embodiments, human monoclonal antibodies against Claudin18.2 may be generated using transgenic or transchromosomal mice carrying a portion of the human immune system rather than the mouse system, and these transgenic and transchromosomal mice include mice referred to as HuMAb mice and KM mice, respectively. In some embodiments, mice are immunized with conjugated peptide expressed by vectors of Claudin18.2 sequences, enriched preparations of recombinantly expressed Claudin18.2 antigen or fragments thereof, and/or cells expressing Claudin18.2 or fragments thereof. Mice can also be immunized with DNA encoding full-length human Claudin18.2 or fragments thereof. When immunizing with purified or enriched preparations of Claudin18.2 antigens and no antibody is produced, mice can be immunized with cells expressing Claudin18.2 (e.g., cell lines) to promote an immune response. Immune response can be monitored throughout immunization with plasma and serum samples obtained from tail vein or retro-orbital blood sampling. Mice with anti-Claudin18.2 immunoglobulin of sufficient titer can be used for fusion. Immunization can be enhanced with Claudin18.2 expressing cells intraperitoneally or intravenously 3 to 5 days prior to mouse execution and removal of the spleen to increase the rate of hybridomas that secrete specific antibodies. In some embodiments, to prepare hybridomas with monoclonal antibodies to Claudin18.2, cells can be isolated from lymph nodes, spleen or bone marrow of immunized mice and fused with an appropriate immortal cell line (e.g., mouse myeloma cell line), and then screened for specific antibodies against the antigen to obtain hybridomas. Next, antibody-secreting hybridomas are screened by ELISA. Antibodies that specifically bind Claudin18.2 are identified by immunofluorescence or FACS analysis. The hybridomas secreted the antibodies can be re-plated and screened again, and if the anti-Claudin18.2 monoclonal antibodies are still positive then subcloning can be performed by limited dilution. Stable subclones are cultured in vitro to produce antibodies in tissue culture medium for characterization. In some embodiments, antibodies are produced in transfected tumors of host cells, for example using a combination of recombinant DNA techniques and gene transfection methods well known in the art (Morrison, S. (1985) Science 229:1202).

In some embodiments, a target gene (e.g., an antibody gene) may be linked into an expression vector (e.g., a eukaryotic expression plasmid). The purified plasmid with the cloned antibody gene may be introduced into eukaryotic host cells, such as CHO cells, NS/0 cells, HEK293T cells or HEK293 cells, or other eukaryotic cells, such as cells from plants, fungi or yeast cells. The methods used to introduce these genes can be those already described in the art, such as electroporation, lipofectine, lipofectamine, or others. After the introduction of these antibody genes into the host cells, the cells expressing the antibodies can be identified and selected. Recombinant antibodies can be isolated and purified from these culture supernatants and/or cells. Antibody genes can also be expressed in other expression systems, including prokaryotic cells such as microorganisms, for example, *Escherichia coli* (*E. coli*). In addition, antibodies can also be produced in non-human transgenic animals, for example in the milk of sheep and rabbits or in eggs, or in transgenic plants, see for example Verma, R., et al. (1998) J. Immunol. Meth. 216:165-181; Pollock, et al. (1999) J. Immunol. Meth. 231:147-157 and Fischer, R., et al. (1999) Biol. Chem. 380:825-839.

As used herein, "antigen" refers to a substance comprising an epitope, and elicits and/or generates an immune response against said epitope. Antigens can include peptides, proteins, glycoproteins, polysaccharides, and lipids, portions thereof, and combinations thereof. Non-limiting exemplary antigens include tumor antigens or pathogenic antigens. The term "antigen" may also refer to a molecule that triggers an immune response. Such an immune response may involve antibody production or activation of specific immunologically active cells, or both. It will be understood by those skilled in the art that any macromolecule, including virtually all proteins or peptides, can be used as an antigen.

The term "epitope" refers to the antigenic determinant cluster in a molecule, i.e., the part of the molecule that is recognized by the immune system (e.g., by an antibody).

Claudin proteins are a family of proteins that are the most important components of tight junctions, in tight junctions, they form the paracellular barrier, and controls the flow of molecules in the intercellular space between epithelial cells. Claudin proteins are transmembrane proteins that cross membrane for four times, with both their N-terminal and C-terminal ends located in the cytoplasm. In some embodiments, the terms "Claudin protein 18" or "CLDN18" or "Claudin 18" or "CLD18" refers to human CLDN18 and include any splice variants thereof, for example, Claudin 18.1 and Claudin 18.2 of CLDN18. In some embodiments, Claudin 18.1 is a peptide with a Genbank accession number of NP_057453 (mRNA: NM_016369). In some embodiments, Claudin 18.1 is a peptide comprising an amino acid sequence of SEQ ID NO: 1 (MSTTTCQVVAFLLSILGLAGCIAATGMDMWSTQDLYDNPVTSVFQYEGLWR SCVRQSSGFTECRPYFTILGLPAMLQAVRALMIVGIVLGAIGLLVSIFA LKCIRI GSMEDSAKANMTLTSGIMFIVSGLCAIAGVSVFANMLVTNFWMSTANMYTG MGGMVQTVQTRYTFGAALFVGWVAGGLTLIGGVMMCIACRGLAPEETNYK AVSYHASGHSVAYKPGGFKASTGFGSNTKNKKIYDGGARTEDEVQSYPSKHD YV) or a protein/peptide comprising a variant of the amino acid sequence. The Claudin 18.2 is a peptide with Genbank accession number NP_001002026 (mRNA: NM_001002026). In some embodiments, the Claudin 18.2 is a peptide comprising the amino acid sequence of SEQ ID NO:2 (MAVTACQGLGFVVSLIGIAGIIAATCMDQWSTQDLYNNPVTAVFNYQGL WRSCVRESSGFTECRGYFTLLGLPAMLQAVRALMIVGIVLGAIGLLVSIFAL KCIRIGSMEDSAKANMTLTSGIMFIVSGLCAIAGVSVFANMLVTNFWMSTA NMYTGMGGMVQTVQTRYTFGAALFVGWVAGGLTLIGGVMMCIACRGLA PEETNYKAVSYHASGHSVAYKPGGFKASTGFGSNTKNKKIYDGGARTEDE VQSYPSKHDYV) or a protein/peptide comprising a variant of the amino acid sequence. The term "variant" refers to mutants, splice variants, conformational, isotypic, and allelic variants, species variants and species homologs, in particular naturally occurring variants. Allelic variants involve alterations in the normal sequence of a gene and their significance is usually insignificant. Whole genome sequencing usually identifies a large number of allelic variants of a given gene. Interspecies homologs are nucleic acids or amino acid sequences that have a different species origin than the given nucleic acid or amino acid sequence. The terms "CLDN", "CLDN18", "Claudin18.1" and "Claudin 18.2" should cover any variants with post-translational modifications and conformational variants. Claudin 18.1 and Claudin 18.2 differ in the N-terminal portion containing the first transmembrane (TM) region and loop 1, while the C-terminal protein primary sequences are identical.

Claudin18.2 is selectively expressed in normal gastric mucosal epithelial cells. The Claudin18.2 expression is restricted to differentiated short-lived gastric epithelial cells and is expressed in a variety of tumor cells. In some embodiments, the primary tumor refers to gastric cancer, esophageal cancer, pancreatic cancer, lung cancer such as non-small cell lung cancer, ovarian cancer, colon cancer, liver cancer, head and neck cancer, and biliary system cancer. In some embodiments, a cell expressing Claudin18.2 refers to a tumor cell, particularly a cell selected from a gastric cancer cell, an esophageal cancer cell, a pancreatic cancer cell, a lung cancer cell, an ovarian cancer cell, a colon cancer cell, a liver cancer cell, a head and neck cancer cell, and a biliary system cancer cell. In some embodiments, a cell expressing Claudin18.2 is a cell in which Claudin18.2 is located at or bound to the cell membrane.

Immunohistochemistry (IHC) is a method for detecting antigens (e.g., proteins) in cells of tissue sections and is widely used to detect abnormal cells, such as tumor cells. The detection antibodies used may bind enzymes, such as peroxidases that catalyze color-producing reactions. Detection antibodies can also be labeled with fluorophores, such as fluorescein or rhodamine. In the present invention, Claudin18.2 expressions in cells are determined by immunohistochemistry. Paraformaldehyde or acetone-fixed cryosections or paraformaldehyde-fixed paraffin-embedded tissue sections taken from non-cancerous or cancerous tissue samples from routine surgery of tumor patients or sections taken from xenograft tumor-bearing mice expressing Claudin18.2 are used. The sections were incubated with Claudin18.2 antibody followed by incubation with goat anti-mouse or goat anti-rabbit antibody conjugated with horseradish peroxidase to perform immunostaining. In this assay, sample preparation is critical to maintain cell morphology, tissue structure, and antigenicity of target antigen epitopes. Paraformaldehyde is usually used to fix the tissue. Depending on the purpose of the test and the thickness of the test sample, thin (approximately 4 to 40 μm) sections are cut from the fixed tissue or used as a whole if the tissue is not very thick and is penetrable. Sections are usually sliced by using a microtome and mounting the sections on a microscope slide. Samples may require optimal processing, including de-paraffinization and antigen retrieval. Usually, a detergent (e.g., Triton X-100) is used in immunohistochemistry to reduce surface tension and the related reagents provide better and more uniform coverage of the sample. Immunohistochemical staining can be performed using a labeled antibody that binds directly to the antigen being stained. Immunohistochemical staining is more commonly done indirectly, using an antibody against the antigen to be detected and a secondary labeled antibody against the primary antibody. The sample is incubated with a blocking buffer (e.g., normal serum, skim milk powder, BSA or gelatin, and commercially available blocking buffers) to block the reaction sites to reduce background staining in IHC. The primary antibody is directed against the target antigen and is usually unlabeled, and the secondary antibody is directed against the immunoglobulin of the primary antibody. The secondary antibody is usually conjugated to a linker molecule (e.g., biotin), which then recruits the reporter, or the secondary antibody is conjugated directly to the reporter itself. The most commonly used assays are the enzyme-mediated chromogenic assay and the fluorophore-mediated fluorescence assay, respectively. The enzyme label reacts with the substrate to produce an intensely colored product that can be analyzed by ordinary light microscopy. Alkaline phosphatase (AP) and horseradish peroxidase (HRP) are two of the most widely used enzymes as labels for protein detection. A variety of chromogenic substrates, fluorescent substrates and chemiluminescent substrates can be used with the enzymes, including DAB or BCIP/NBT. Fluorescent reporters are small organic molecules used in IHC assays. For chromogenic and fluorescent assays, optical density analysis of the signal provides semi-quantitative and full quantitative data, respectively, correlating the level of the reporter signal with the level of protein expression or localization. After immunohistochemical staining of the target antigen, a second stain (e.g., hematoxylin, Hoechst stain, and DAPI) is often performed to provide contrast that helps highlight the first stain.

The present invention provides methods for detecting the presence of a Claudin18.2 antigen in a sample or for measuring the amount of a Claudin18.2 antigen in a sample. When the antibody forms a complex with the Claudin18.2 antigen, contacting the sample (or the control sample) with the antibody of the present invention that binds to Claudin18.2 antigen. Then detecting the formation of the complex, and by comparing the difference between the complex formed in the sample and the complex formed in the control sample, the presence of the Claudin18.2 antigen in the sample is determined. The detecting method of the present invention may be used in particular for diagnosing Claudin18.2 related diseases, such as tumors. In some embodiments, the amount of the Claudin18.2 antigen in a sample is higher than the amount of the Claudin18.2 antigen in a reference or control sample indicating that an individual (in particular a human) from which said sample originated has a Claudin18.2-related disease, such as a tumor. In some embodiments, said measured sample is a cellular sample, such as a sample comprising cells (e.g., tumor cells). Said complex is formed by the antibody, antigen-binding fragment or conjugate of the invention and the Claudin18.2 expressed by the cells in the above mentioned sample.

A "reference" in the present invention (e.g., a reference sample or reference organism) may be used to correlate and compare with results obtained by the method of the present invention from a test sample or a test organism. Said reference organism is generally a healthy organism, in particular an organism not suffering from a disease (such as a tumor). The "reference value" or "reference level" may be determined empirically by measuring a sufficiently large number of reference organisms based on the reference organism. Preferably, the reference value is determined by measuring at least 2, preferably at least 3, preferably at least 5, preferably at least 8, preferably at least 12, preferably at least 20, preferably at least 30, preferably at least 50, or preferably at least 100 references.

The term "nucleic acid" refers to deoxyribonucleic acid (DNA) or ribonucleic acid (RNA), including genomic DNA, cDNA, mRNA, recombinantly prepared or chemically synthesized molecules. Nucleic acids may be in the form of single- or double-stranded molecules or may be linear or covalently closed circular. RNA includes double-stranded RNA, single-stranded RNA, isolated RNA (e.g., partially purified RNA), substantially pure RNA, synthetic RNA, recombinantly produced RNA, and modified RNA that differs from natural RNA by addition, deletion, substitution, and/or alteration of one or more nucleotides. RNA can be modified by sequence stabilization, cap addition, and polyadenylation. The term "transcription" refers to the process in which the genetic code in a DNA sequence is transcribed into RNA. The terms "nucleic acid molecule code", "coding DNA sequence" and "coding DNA" refer to the order or sequence of deoxyribonucleotides along the deoxyribonucleic acid chain. The order of these deoxyribonucleotides determines the order of the amino acids along the polypeptide (protein) chain. Thus, the nucleic acid sequence encodes the amino acid sequence. The term "homologous" refers to nucleic acids that are naturally associated in function, while the term "heterologous" refers to nucleic acids that are not associated naturally in function. In some embodiments, the nucleic acid may be associated to a homologous or heterologous expression control sequence in function.

The term "expression" includes the generation of RNA or RNA and protein/peptide. In the case of RNA, the term "expression" or "translation" refers specifically to the production of a peptide or protein. Expression may be transient or stable. Expression also includes aberrant or abnormal expression, i.e., altered (e.g., increased) expression compared to a reference (e.g., an individual without a disease associated with aberrant or abnormal expression of certain proteins (e.g., tumor-associated antigens). Increased expression means an increase of at least 10%, in particular at least 20%, at least 50% or at least 100% or more. In one embodiment, expression is seen only in diseased tissues, while expression is suppressed in healthy tissues. Specific expression refers to that the protein is expressed essentially only in specific tissues or organs. For example, a tumor-associated antigen that is specifically expressed in the gastric mucosa means that the protein is expressed primarily in the gastric mucosa and not in other tissues or is not significantly expressed in other tissues or organ types. In some embodiments, the tumor-associated antigen is specifically expressed in more than one normal tissue type or organ (e.g., in no more than 3 different tissues or organ types), then the tumor-associated antigen may be considered to be specifically expressed in those organs.

As used herein, the term "isolated" means isolated from cellular components or other components in which polynucleotides, peptides, polypeptides, proteins, antibodies or fragments thereof are usually associated in their natural state. Non-naturally occurring polynucleotides, peptides, polypeptides, proteins, antibodies, or fragments thereof do not require to be "isolated" to distinguish them from their naturally occurring counterparts. Isolated nucleic acid means that the nucleic acid is (i) amplified in vitro, e.g., by polymerase chain reaction (PCR), (ii) generated by clonal recombination, (iii) purified, e.g., by cleavage and gel electrophoresis grading, or (iv) synthesized, e.g., by chemical synthesis. The isolated nucleic acid is nucleic acid that can be manipulated by recombinant DNA techniques. An isolated protein or isolated peptide is a protein or peptide that has been isolated from its natural environment, substantially free of other substances to which it is bound in nature or in vivo. In addition, "concentrated", "isolated" or "diluted" polynucleotides, peptides, polypeptides, proteins, antibodies or fragments thereof can be distinguished from their naturally occurring counterparts because the concentration or amount of molecules per volume is greater ("concentrated") or less ("diluted") than the concentration of their naturally occurring counterparts. In some embodiments, the technical solutions of the present invention preferably have a higher degree of enrichment. Thus, for example, preferably a 2-fold enrichment, more preferably a 10-fold enrichment, more preferably a 100-fold enrichment, more preferably a 1000-fold enrichment. It can also provide "isolated" materials by means of artificial assembly, for example by chemical synthesis or recombinant expression.

The term "variant" includes mutants, splice variants, conformational, isotypic, and allelic variants, species variants and species homologs, in particular naturally occurring ones. Allelic variants refer to alterations in the normal sequence of a gene, the significance of which is usually insignificant. Whole genome sequencing usually identifies a large number of allelic variants of a given gene. Interspecies homologs are specified nucleic acid or amino acid sequences that have different species origins.

The term "amino acid modification" (or modified amino acids, variants of amino acid sequences) includes amino acid substitutions, insertions and/or deletions of specific amino acid sequences that produce sequences functionally equivalent to said specific sequences. In some embodiments, the amino acid-modified antibody remains bound to its target antigen. Thus, one or more amino acid residues in the CDR region or in the framework region of the antibody of the present invention can be replaced with other amino acid residues of similar side chains. Preferably, the sequences of the CDR sequence, the sequences of the high variable region and the variable region of the antibody are modified without losing the ability to bind the target antigen. Amino acid variants can be readily prepared by those of skill in the art by recombinant RNA manipulation. For example, DNA sequence manipulations for preparing proteins and peptides with substitutions, additions, insertions, or deletions are described in detail in Sambrook et al. (1989). In addition, the peptides and amino acid variants described herein can be readily prepared with known peptide synthesis techniques (e.g., solid-phase synthesis and similar methods). For example, only those with 1 to 5, 1 to 4, 1 to 3, or 1 or 2 substitutions are considered to be highly homologous. Amino acid deletion variants that contain a deletion at the N and/or C termini of the protein are referred to as N and/or C termini truncated variants. Amino acid addition variants contain amino and/or carboxyl termini fused to one or more amino acids, such as 1, 2, 3, 5, 10, 20, 30, 50 or more amino acids. The amino acid deletion variant is the removal of one or more amino acids from the sequence (e.g., the removal of 1, 2, 3, 5, 10, 20, 30, 50, or more amino acids). Amino acid substitution variants are those in which at least one amino acid residue is removed from sequence and another amino acid residue is inserted in its place. In one embodiment, a non-conserved amino acid residue between homologous proteins or peptides is modified and/or replaced with an amino acid residue of similar properties. Preferably, similarity or identity between the amino acid sequence and the amino acid sequence of its amino acid sequence variant is preferably at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99 percent. Preferably, the similarity or identity is directed to an amino acid region is at least about 10%, at least about 20%, at least about 30%, at least about 40%, at least about 50%, at least about 60%, at least about 70%, at least about 80%, at least about 90%, or about 100% of the full length of the reference amino acid sequence. For example, if the reference amino acid sequence consists of 200 amino acids, preferably similarity or identity is given for at least about 20, at least about 40, at least about 60, at least about 80, at least about 100, at least about 120, at least about 140, at least about 160, at least about 180, or about 200 amino acids, preferably contiguous amino acids. In some preferred embodiments, the similarity or identity is given for the full-length reference amino acid sequence. Alignment for determining sequence similarity (preferably sequence identity) can be performed with tools known in the art, preferably using optimal sequence alignment, for example using Align, adopting standard settings, preferably EMBOSS; needle; Matrix; Blosum62; Gap Open 10.0; Gap Extend 0.5. Sequence similarity refers to the percentage of amino acids that are identical or represent conservative amino acid substitutions. The identity of two amino acid sequences refers to the percentage of amino acids that are identical between the two sequences, this percentage is completely statistically significant and the differences between the two sequences are randomly distributed over their full length. Sequence alignment can be performed with the followings: the local homology algorithm of Smith and Waterman, 1981, Ads App. Math. 2, 482, the local homology algorithm of Neddleman and Wunsch, 1970, J. Mol. Biol. 48, 443, the similarity search methods of Pearson and Lipman, 1988, Proc.Natl Acad.Sci.USA 85, 2444, or computer programs using these algorithms (GAP, BESTFIT, FASTA, BLAST P, BLAST N, and TFASTA in the Wisconsin Genetics package, Genetics Computer Group 575ScienceDrive, Madison, Wis.).

The term "peptide" includes oligopeptides and polypeptides and refers to substances comprising two or more, preferably 3 or more, preferably 4 or more, preferably 6 or more, preferably 8 or more, preferably 9 or more, preferably 10 or more, preferably 13 or more, preferably 16 or more, preferably 21 or more, and up to preferably 8, 10, 20, 30, 40 or 50 (in particular 100) amino acids covalently linked by peptide bonds. The term "protein" refers to a large peptide, preferably a peptide having more than 100 amino acid residues, and generally the terms "peptide" and "protein" are synonymous and are used interchangeably herein.

"Derivatives" of proteins and peptides are modified forms of proteins and peptides. Such modifications include any chemical modification and include single or multiple substitutions, deletions and/or additions of any molecule (e.g., carbohydrate, lipid and/or protein or peptide) associated with the protein or peptide. A "derivative" of a protein or peptide includes a modified analog and all functional chemical equivalents that are glycosylated, acetylated, phosphorylated, amidated, palmitoylated, myristoylated, prenylated, lipidated, alkylated, derivatized, introduced with a protecting/blocking group, proteolytically cleaved or bound to antibodies or other cellular ligands, and all the functional chemical equivalents. In some embodiments, the stability and/or immunogenicity of the modified peptide is enhanced.

The term "cell" refers to a cell with an intact membrane that has not yet released its normal intracellular components (e.g., enzymes, organelles, or genetic material), preferably a viable cell, i.e., a living cell capable of carrying out its normal metabolic functions. It includes prokaryotic cells (e.g., *E. coli*) or eukaryotic cells (e.g., dendritic cells, B cells, CHO cells, COS cells, K562 cells, HEK293 cells, HELA cells, yeast cells, and insect cells). Preferably, the cells are mammalian, such as cells from human, mouse, hamster, pig, goat, and primates. The cells may be derived from a large number of tissue types and include primary cells and cell lines. In some embodiments, the cells include non-cancer cells and cancer cells. A target cell is a cell that is the target of an immune response, such as a tumor cell as described herein. In some embodiments, the target cell is a cell expressing Claudin18.2. In some embodiments, the cells expressing Claudin18.2 usually comprise cancer cells.

The reagents, compositions and methods herein can be used to diagnose whether an individual has a disease. The diseases that may be diagnosed cover all diseases expressing Claudin18.2, preferably tumors, such as gastric cancer, pancreatic cancer, esophageal cancer, ovarian cancer, biliary system cancer, etc.

The term "disease" refers to any pathological state, including tumors, particularly those types of tumors described herein.

The term "normal" as used in the term "normal tissue" or "normal condition" refers to a condition in a healthy tissue or healthy individual, i.e., a non-pathological condition, where "healthy" is preferably intended to mean non-tumorous.

Herein, "Claudin18.2-associated disease" refers to an elevated expression of Claudin18.2 in cells of a diseased tissue or organ compared to a healthy tissue or organ. By elevated is meant an elevation of at least 10%, in particular at least 20%, at least 50%, at least 100%, at least 200%, at least 500%, at least 1000%, at least 10,000% or even higher. In the context of the present invention, Claudin18.2 related diseases include tumors, in particular those of the types described herein.

"Reduced" herein refers to the ability to reduce Claudin18.2 expression by at least 5% or more, 10% or more, 20% or more, preferably 50% or more and most preferably 75% or more compared to the cells previously detected. The term "suppression" refers to complete or substantially complete suppression, i.e., a reduction to 0 or substantially to 0.

Herein, the terms "cancer" and "tumor" are used interchangeably to refer to diseases in which cells exhibit uncontrolled growth, and/or invasion, and/or metastasis. Examples include leukemia, melanoma, lymphoma, neuroblastoma, glioma, rectal cancer, endometrial cancer, kidney cancer, adrenal cancer, thyroid cancer, blood cancer, skin cancer, brain cancer, cervical cancer, intestinal cancer, liver cancer, colon cancer, stomach cancer, intestinal cancer, head and neck cancer, gastrointestinal cancer, lymph node cancer, esophageal cancer, colorectal cancer, pancreatic cancer, ear, nose and throat (ENT) cancer, breast cancer, prostate cancer, uterine cancer, ovarian cancer, and lung cancer, and the metastases thereof.

The term "metastasis" refers to the spread of cancer cells from their original site to other parts of the body. The formation of metastasis is a very complex process and depends on the detachment of malignant cells from the primary tumor, invasion of the extracellular matrix, penetration of the endothelial basement membrane to enter the body cavity and blood vessels, and subsequent infiltration of target organs by blood transport. Finally, the growth of new tumors (i.e., secondary or metastatic tumors) at the target site is dependent on angiogenesis. Tumor metastasis often occur even after removal of the primary tumor, as tumor cells or components may remain and develop metastatic potential. In one embodiment, metastasis refers to distal metastasis, i.e., metastasis away from the primary tumor and/or local lymph node system. The cells of a secondary or metastatic tumor are similar to the cells in the original tumor.

The term "relapse" or "recurrence" refers to when an individual is affected again by a disorder that he or she had in the past. For example, if an individual has had a disease and has been treated and cured, and then the disease occurs again, the new disease may be considered a recurrence or relapse. Recurrence or relapse of a tumor includes situations where said tumor occurs at a site different from the original tumor as well as at the site of the original tumor.

The term "treatment", means the administration of a compound or composition to an individual to prevent or eliminate a disease, including reducing the size or number of diseases in an individual; stalling or slowing the disease process in an individual; inhibiting or slowing the development of a new disease in an individual; reducing the the symptoms and/or the frequency or severity of recurrence in an individual who currently has or has previously had a disease; and/or prolong (i.e., increase) the life span of an individual. In some embodiments, treatment of a disease includes curing the disease or its symptoms, reducing the duration, mitigating, preventing, slowing or inhibiting the progression or deterioration, or preventing or delaying the onset of a disease.

Herein, the terms "object", "individual", "organism", or "patient" are interchangeable and include vertebrate animals, preferably mammals. In the present invention, mammals are humans, non-human primates, domesticated animals (e.g., dogs, cats, sheep, cattle, goats, pigs, horses, etc.), laboratory animals (e.g., mice, rats, rabbits, guinea pigs, etc.), and captive animals (e.g., zoo animals). As used herein, the term "animal" also includes a human being. The term "subject", "individual" includes a patient, i.e., a diseased animal, preferably a human.

The term "sample" may be any sample available according to the present invention, including biological samples, such as tissue samples (including body fluids) and/or cell samples, which may be obtained in a routine manner, for example by surgery or tissue biopsy (including punch biopsy) and by collection of blood, bronchial aspirates, sputum, urine, excreta or other body fluids. According to the present invention, the term "sample" also includes processed samples, such as biological samples or isolates, such as nucleic acid and peptide/protein isolates and formalin-treated paraffin-embedded tissues. Preferably, the sample comprises cells or tissues of an organ to be tested (e.g., for cancer diagnosis). For example, if the cancer to be diagnosed is lung cancer, the sample may contain cells or tissues obtained from the lung. The sample may be a tissue sample from a patient containing tumor cells or cancer cells or suspected of containing tumor cells or cancer cells, including blood, body fluids, a primary tumor or tissue samples obtained from or tumor metastasis, or any other sample containing tumor cells or cancer cells.

In one aspect, the present invention provides an antibody or antigen-binding fragment capable of recognizing an antigenic peptide comprising the sequence shown in SEQ ID NO: 7 (KNKKIYDGG); and also an antibody or antigen-binding fragment capable of recognizing an epitope comprising the sequence shown in SEQ ID NO: 7 in Claudin 18.2.

In one aspect, the present invention provides an antibody or antigen-binding fragment capable of recognizing an antigenic peptide comprising the sequence shown in SEQ ID NO: 6 (KNKKIYDGGART); and also an antibody or antigen-binding fragment capable of recognizing an epitope comprising the sequence shown in SEQ ID NO: 6 in Claudin18.2.

In one aspect, the present invention provides an antibody produced by a hybridoma cell line (also referred to as hybridoma cell line 9G5) deposited under the accession number CCTCCNO.C202007 or CCTCCNO.C202008. The antibody produced by the hybridoma cell line (also known as hybridoma cell line 14F8) deposited under CCTCCNO.C202007 is called antibody 9, and the antibody produced by the hybridoma cell line deposited under CCTCCNO.C202008 is called antibody 7, both are deposited at the China Center For Type Culture Collection, Wuhan University, Wuhan, China, Wuhan, post code 430072, China.

In one aspect, the present invention provides a composition (e.g., diagnostic composition) or assay kits comprising an antibody or antigen-binding fragment, or a combination of antibodies and/or antigen-binding fragments as described herein. The diagnostic composition or assay kit may be used in the method of the present invention, such as the method of the present invention for diagnosis, detection, or monitoring. These kits optionally comprise a detectable label, such as an indicator enzyme, a radiolabeler, fluorophores or paramagnetic particles. The kits optionally comprises an informational manual, for example, a manual for describing how to use the reagents to implement the method disclosed herein.

When used in the methods described above, the antibody described herein may be provided with a label that performs the function of the following: (i) providing a detectable signal; (ii) interacting with a second label to modify the detectable signal provided by the first or second label, such as FRET (Fluorescence Resonance Energy Transfer); (iii) affecting the mobility (e.g., electrophoretic mobility) by charge, hydrophobicity, shape, or other physical parameters, or (iv) providing a capture component, such as affinity, antibody/antigen, or ion complexation.

Those suitable as labels are structures as follows: such as fluorescent labels, luminescent labels, chromophore labels, radioisotope labels, isotope labels, preferably stable isotope labels, isobaric labels, enzyme labels, particle labels (especially metal particle labels, magnetic particle labels, polymeric particle labels), small organic molecules (such as biotin, ligands for receptors, or binding molecules (such as cell adhesion proteins or lectins)), label sequences comprising nucleic acid and/or amino acid residues detectable by using binding agents, etc. Labels include, non-limitingly, barium sulfate, iocetamic acid, iopanoic acid, calcium ipodate, diatrizoate sodium, meglumine diatrizoate, metrizamide, tyropanoate sodium, and radiodiagnostic agents (including positron emitters, (e.g., fluorine-18 and carbon-11), gamma emitters (e.g., iodine-123, technetium-99m, iodine-131, and indium-111), the nuclear magnetic resonance nuclides (e.g., fluorine and gadolinium)).

"At risk" means a subject (i.e., a patient) who is identified as having a higher than normal chance of developing a disease (e.g., cancer) compared to common population. In addition, a subject who has or currently has a disease (especially cancer) is a subject with an elevated risk of disease occurrence because the subject may continue to develop the disease. A subject who currently has or has had cancer also has an elevated risk of cancer metastasis.

Also involved herein is a method for diagnosing, detecting or monitoring cancer, wherein the method comprises: contacting a sample to be tested with the antibody or antigen-binding fragment, or the conjugate of the present invention; and detecting the amount the complex formed by the antibody or antigen-binding fragment, or the conjugate and Claudin 18.2. The method can be used to detect whether the subject has a tumor or is at risk of developing a tumor, or whether the subject has cancer disease or is at risk of developing cancer disease. In one embodiment, the sample for measuring is a tissue or cell sample, such as a sample comprising cells (e.g., tumor cells). The complex is formed between an antibody, antigen-binding fragment or conjugate of the present invention and Claudin18.2 expressed by the cells in the sample.

In the method for diagnosing and detecting cancer described herein, the antibody or antigen-binding fragment, or the conjugate of the invention is reacted with a cell sample, a normal sample (or a control sample) taken from a subject, respectively, and when the amount of the complex obtained by reaction with the cell sample of the subject is significantly higher than the amount of the complex obtained by reaction with the normal sample (or the control sample), it indicates that the subject may have cancer. Normal samples and significantly elevated are defined as described above herein.

In the method for monitoring cancer described herein, for a subject, at two time points separated by a period of time, such as a first time and a second time, the amount of complexes formed by cells expressing Claudin 18.2 and the antibody or antigen-binding fragment, or the conjugate in a first sample (obtained at the first time) and a second sample (obtained at the second time) respectively from the subject is measured, and by the difference between the amounts of the complexes in the two detections, changes of the subject's cancer disease, such as regression, progression, etc. are evaluated.

For example, a detection result showing a significant reduction in complex formation in the second sample compared to the first sample obtained at the first time may indicate regression of the subject's cancer or tumor or a reduced risk of disease. For example, a detection result showing a significant increase in complex formation in the second sample compared to the first sample obtained at the first time may indicate an increased risk of metastasis, recurrence or disease of the subject's cancer or tumor.

Also involved herein is a method for analyzing whether a tumor can be treated by a tumor therapy targeting Claudin18.2, wherein the method comprises: (i) contacting a sample comprising tumor cells with the antibody or antigen-binding fragment herein, or with the conjugate herein; (ii) detecting the amount of the complex formed between the antibody or antigen-binding fragment, or the conjugate and Claudin18.2.

wherein, in one specific embodiment, the tumor cells are gastric cancer cells, esophageal cancer cells, pancreatic cancer cells, lung cancer cells, ovarian cancer cells, colon cancer cells, liver cancer cells, head and neck cancer cells, or biliary system cancer cells; preferably, the tumor cells are gastric cancer cells, esophageal cancer cells, pancreatic cancer cells, or biliary system cancer cells. In one embodiment, the complex is formed between the antibody, antigen-binding fragment, or conjugate and Claudin18.2 expressed by cancer cells in a sample from a subject.

In the analytical method described herein, for a same subject, at two time points before and after a targeted therapy, such as a first time point (before the targeted therapy) and a second time point (after the targeted therapy), the amount of complex formed by the cells expressing Claudin18.2 and the antibody or antigen-binding fragment, or the conjugate in the first sample (obtained at the first time) and the second sample (obtained at the second time) from the subject, respectively. And by the difference between the amount of the complexes in the two detections, whether the subject can be treated by a tumor therapy targeting Claudin18.2 is evaluated.

In one aspect, the present invention provides a kit comprising the antibody or antigen-binding fragment or the combination of the antibody and/or antigen-binding fragments as described herein. The kit may be used in the methods of the present invention, such as the methods of the present invention for diagnosis, detection or monitoring. The kit optionally comprise detectable labels, such as indicator enzymes, radioactive labels, fluorophores or paramagnetic particles. The kit can comprise an informative manual, for example, a manual for describing how to use the reagents to implement the methods disclosed herein.

EXAMPLE

The present invention is further described below in combination with specific examples. It should be understood that these examples are intended to illustrate the invention only and are not intended to limit the scope of the invention. Experimental methods for which specific conditions are not indicated in the following examples generally follow conventional conditions such as those described in J. Sambrook et al., eds., Molecular cloning: A Laboratory Manual, Third Edition, Science Press, 2002, or as recommended by the manufacturer.

Example 1. Antibody Screening

In vitro synthesis of Claudin18.2 C-terminal polypeptide (methionine at position 191—valine at position 261, see SEQ ID NO:3) as an immunogen.

The sequence of SEQ ID NO:3 is shown as below.

```
MMCIACRGLAPEETNYKAVSYHASGHSVAYKPGGFKASTGFGSNTKNK

KIYDGGARTEDEVQSYPSKHDYV
```

Next, 6-8 weeks old female Balb/C mice are selected for immunization: immunogen is mixed 1:1 with Freund's adjuvant or Gerbu MM adjuvant, the immunization dose is (50-100 μg)/mouse and is immunized subcutaneously or intraperitoneally every other week or every two weeks for a total of three or four times. Two days before splenectomy, mice are booster immunized. Splenocytes from immunized mice are isolated and fused with mouse myeloma cells SP2/0 (ATCC, CRL 1581) according to a public standard protocol (Kohler, Milstein, 1975). After screening and culturing in HAT medium, by detecting the hybridoma supernatant with ELISA, a total of 139 positive clones are obtained, among which 11 are strong positive clones.

These 11 candidate antibodies are expressed by serum-free culture, and the 11 candidate antibodies are prepared by Protein G purification and named as antibody 1, antibody 2, antibody 3, antibody 4, antibody 5, antibody 6, antibody 7, antibody 8, antibody 9, antibody 10, and antibody 11, respectively, for subsequent detection. The obtained 11 antibodies are identified with Western Blot, and the binding to 293T-Claudin18.2 and 293T-Claudin18.1 cell lysates is detected. Western procedure is: extracted the total protein (Beyoncé, P0013B) of 293T-Claudin18.1, 293T-Claudin18.2 cells with RIPA lysate (strong), and after the protein is quantified, they are loaded at 30 μg/well and ran the gel at a constant pressure in a 12% separation gel, followed by membrane transfer at a constant current of 200 mAh for 1 h, blocking with 5% skim milk powder and then sequentially adding primary antibody (10 μg/mL) Claudin18 Polyclonal Antibody 1:200 dilution (Thermo Fisher, CAT 38-8000 or anti-flag-HRP 1:500 dilution or Anti-Claudin18.2 antibody [EPR19202-244] 1:200 dilution (Abcam, ab222512); secondary antibodies (sheep anti-mouse IgG-HRP 1:1000, sheep anti-rabbit IgG-HRP 1:1000), and incubating. After the membrane is thoroughly washed and then imaged and photographed under a chemiluminescent imager. B-actin is used as the internal reference control. The detection results are shown in FIG. 2A and FIG. 2B.

Based on the detection results, seven candidate antibodies are selected for further screening by immunohistochemistry. And two strains of hybridomas, antibody 7 and antibody 9, are selected for strain deposit. The deposit information is: the two strains of hybridoma cells are deposited at the China Center For Type Culture Collection (Wuhan, China), the names and accession numbers are as follows: antibody 7 (also known as antibody 9G5), deposit number: CCTCCNO.C202008, deposit date: Jan. 3, 2020. Antibody 9 (also known as antibody 14F8), deposit number: CCTCCNO.C202007, deposit date: Jan. 3, 2020.

Example 2. Histological Analysis 7 antibodies (antibody 5, antibody 6, antibody 9, antibody 11, antibody 4, antibody 8 and antibody 7) are screened from the 11 antibodies. The tissue specificity of the binding capacity of these antibodies to their antigens in formalin-fixed paraffin-embedded tissues (FFPE) is evaluated by immunohistochemistry.

The sequence of the control antibody H-43-14A_2 (also referred to as 43-14A2 herein) is from patent CN104321345A, and the sequence of the light chain variable region is shown in SEQ ID NO: 4 (divmtqaafsipvtlgt-sasiscrssknllhsdgitylywylqrpgqspqlliyrvsnlasgvpnrfsgs-esgtdftlri srveaedvgvyycvqvlelpftfgggtkleikr), and the sequence of the heavy chain variable region is shown in SEQ ID NO: 5 (iqlvqsgpelkkfgetvkisck-asgytftdysihwvkqapgkglkwmgwintetgvptyaddfkgrfafslet-sastay lqinnlknedtatyfcarrtgfdywgqgttltvss). With the method of in vitro recombinant expression, a murine monoclonal antibody comprising the variable regions of the light and heavy chain of the antibody is prepared. The control antibody EPR19202-244 is obtained from Abcam.

Immunohistochemistry method: immunohistochemistry (IHC) is performed on microscope slides of formalin-fixed paraffin-embedded samples. After the microscope slides are deparaffinized, they are incubated with 3% hydrogen peroxide at room temperature and then placed in boiling pH 9.0 Tris buffer for 10 min in a microwave for antigen retrieval, followed by incubating with 0.2-2 μg/mL of Claudin18.2 antibodies (antibody 4, antibody 5, antibody 6, antibody 7, antibody 8, antibody 9, and antibody 11) and 43-14A2 overnight at 4° C. Using a polymer-based antibody (Dako REAL™ En Vision™ Detection System, Peroxidase/DAB+, Rabbit/Mouse) and a substrate developer (Dako REAL™ En Vision™ Detection System, Peroxidase/DAB+), and the antibody binding are visualized using horseradish peroxidase-conjugated secondary antibodies. They are then re-stained with hematoxylin and then evaluated by an evaluator.

Stomach and lung tissue sections from rhesus monkeys (Rhesus monkey Genbank accession number XP 001114708.1, the homology with the sequence of human CLDN18.2 (NP_001002026.1) is 98.85%) are stained with antibody 4, antibody 5, antibody 6, antibody 7, antibody 8, antibody 9, antibody 11, and 43-14A2, and the staining results are evaluated for specificity; immunohistochemical staining is performed on normal human tissue microarrays to confirm the specificity of the antibodies to the staining results of normal human tissues; immunohistochemical reactions are performed on human gastric and lung cancer sections to confirm the specificity and sensitivity of the antibodies to human tumor tissues; immunohistochemical staining is performed on human gastric cancer tissue microarrays to evaluate the sensitivity of the antibodies.

Histological evaluation: the staining results are evaluated in terms of both staining intensity and stained positive tumor cells %. Staining intensity: Any intensity of cell membrane or cytoplasm staining is considered positive staining, and the staining intensity is classified as negative (−), weakly positive (1+), positive (2+) and strongly positive (3+).

1. Staining of Gastric and Lung Tissue Sections of Rhesus Monkeys with Antibodies The antibody staining results of gastric and lung tissues of rhesus monkeys are shown in Table 1. Antibody 4, antibody 5, antibody 6, antibody 7, antibody 8, antibody 9, and antibody 11 staines the epithelial cells of the gastric mucosa of rhesus monkeys to different degrees, with staining intensity ranging from 1+ to 3+, and a few antibodies produce non-specific staining/background staining; there are negative and positive reactions for lung tissues of rhesus monkeys. Antibody 4, antibody 5, antibody 7, antibody 8 and antibody 9 staines gastric tissues specifically and do not stain lung tissues, while control antibody 43-14A2 staines lung tissues non-specifically; control antibody EPR19202-244 staines gastric tissues specifically with high intensity at the working concentration of 0.37 μg/mL recommended in the instructions and do not stain lung tissues.

TABLE 1

Staining of rhesus monkey stomach and lung tissues with Claudin18.2 antibody

| | | antibody (working concentration is 2 μg/mL) | | | | | | | | Abcam |
|---|---|---|---|---|---|---|---|---|---|---|
| tissue | staining state | antibody 5 | antibody 6 | antibody 9 | antibody 11 | antibody 4 | antibody 8 | antibody 7 | 43-14A2 | EPR19202-244 |
| stomach | Specific staining intensity | 1+ | 2+ | 3+ | 3+ | 2+ | 2+ | 3+ | 3+ | 2+~3+ |
| | Non-specific/ background staining | No | Yes | No | Yes | No | No | No | No | No |
| Lung | Specific staining intensity | 1+ | 1+ | 0 | 0 | 0 | 0 | 0 | 0 | 0 |
| | Non-specific/ background staining | No | Yes | No | Yes | No | No | No | Yes | No |

2. Staining of Normal Human Tissues with Antibody 9

Antibody 9 at working concentration of 0.2 μg/mL, and control antibody EPR19202-244 at a working concentration of 0.37 μg/mL, are respectively used to stain tissue microarrays (Shanghai Outdo Biotech Co., Ltd., microarray number: HorgN090PT02) derived from a total of 24 normal organs (2-6 cases of each, and a point for each case) of 7 normal subjects. Antibody 9 shows positive staining only in epithelial cells of gastric mucosa and negative staining in all other tissues, but EPR19202-244 shows more obvious background staining in skeletal muscle and cardiac muscle tissues. For epithelial cells from 6 cases of gastric mucosa, both antibody 9 and EPR19202-244 shows strong positive staining; EPR19202-244 antibody shows background staining in 1 of 3 cases of cardiac muscles and 1 of 7 cases of skeletal muscles, while antibody 9 shows negative staining in all cases. In the remaining 4 cases of thyroid, 3 cases of tongue, 4 cases of esophageal epithelium, 2 cases of duodenal mucosa, 6 cases of jejunal mucosa, 3 cases of ileal mucosa, 5 cases of appendix, 4 cases of colonic mucosa, 2 cases of rectal mucosa, 2 cases of liver, 2 cases of pancreas, 3 cases of trachea, 5 cases of lung, 3 cases of skin, 1 case of seminal vesicle, 3 cases of prostate, 7 cases of testis, 4 cases of bladder, 1 case of medulla oblongata, 2 cases of telencephalon, 2 cases of cerebellum, 1 case of brainstem, 2 cases of spleen, the two antibodies shows negative staining.

3. Staining of Human Gastric/Lung Cancer Tissues with Antibodies

Antibody 7, antibody 9, control antibody 43-14A2 at a working concentration of 0.2 μg/mL, and control antibody Abcam EPR19202-244 at a working concentration of 0.37 μg/mL as recommended in the instruction, are used to stain tissue samples of human gastric or lung cancer. The main steps of staining are: the tissue sections are deparaffinized and antigen-retrieved, then incubated with CLDN18A2 antibody followed by incubation of the samples with a blocking buffer, then incubated with horseradish peroxidase (HRP)-labeled secondary antibody, and finally the addition of a chromogenic substrate for color development.

Figure 4:
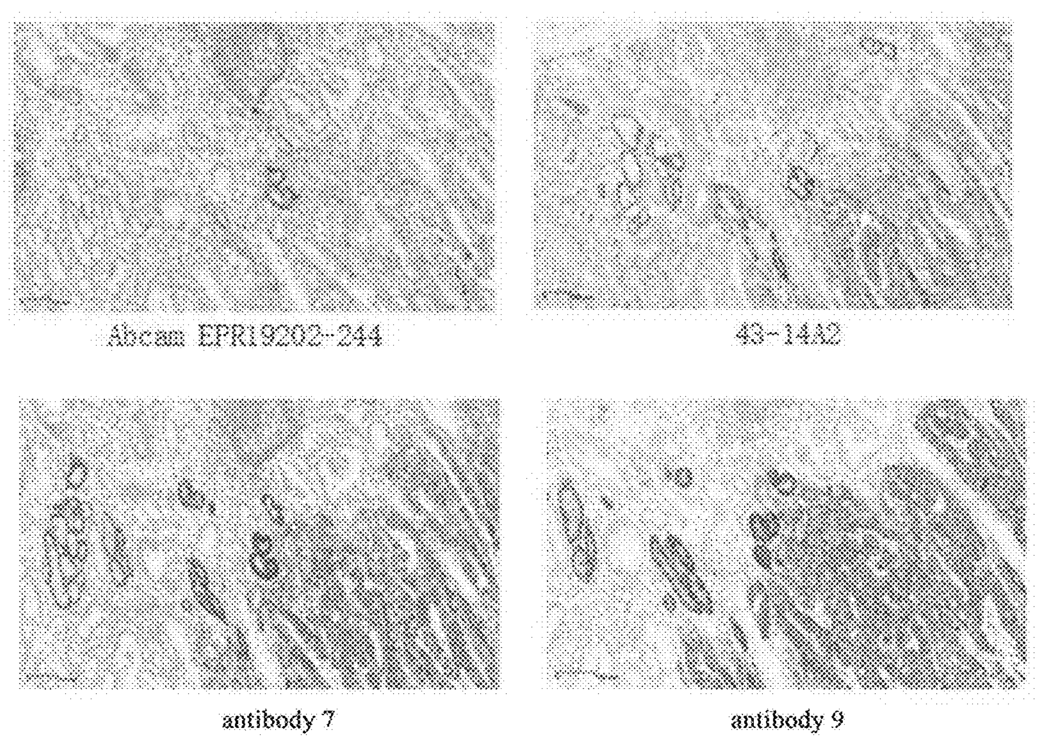
FIG. 4: Results of staining of antibody 7 and antibody 9 on a gastric cancer sample 2018-50829E.
Figure 5:
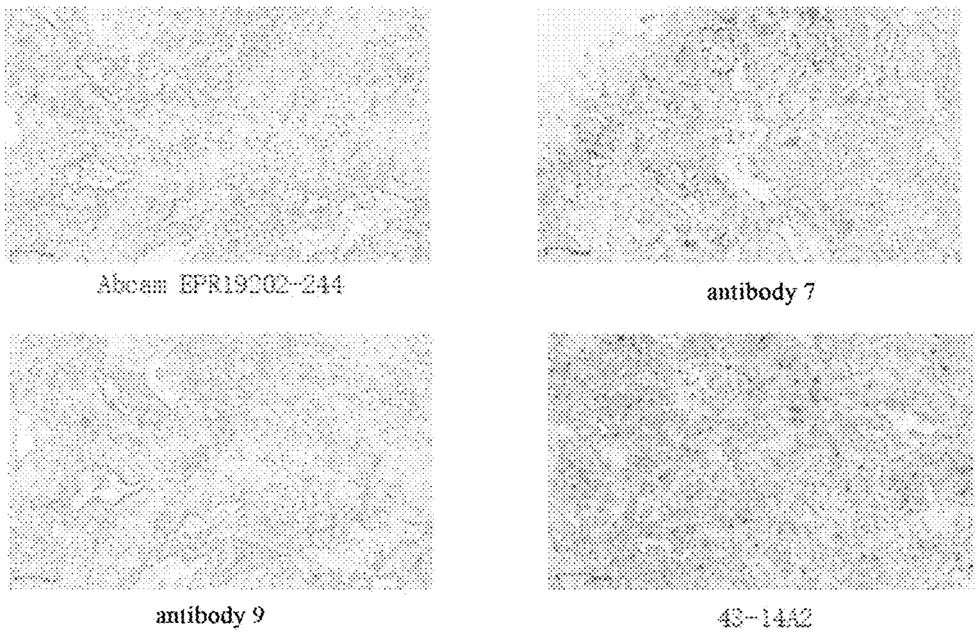
FIG. 5: Results of staining of antibody 7 and antibody 9 on a lung cancer sample 2018-55164F.

The staining results for gastric cancer sample F163060A1 (purchase from Fanpu biotech, Inc., Guilin) are shown in FIG. 3. The staining results for gastric cancer sample 2018-50829E (purchase from Fanpu biotech, Inc., Guilin) are shown in FIG. 4. The staining results for the lung cancer sample 2018-55164F (purchase from Fanpu biotech, Inc., Guilin) are shown in FIG. 5. The statistical results of the staining are shown in Table 2.

TABLE 2

Staining of human gastric/lung cancer tissues with Claudin18.2 antibody

| | | Claudin18.2 diagnostic antibody | | | Abcam |
|---|---|---|---|---|---|
| Tissue | Staining state | antibody 9 | antibody 7 | 43-14A2 | EPR19202-244 |
| Gastric cancer (F163060A1 ) | tumor tissue specific staining intensity | 1+ | 1+ | 1+ | 0 |
| | Non-specific/background staining | No | No | Yes | No |
| Gastric cancer (2018-50829E) | tumor tissue specific staining intensity | 3+ | 2+ | 2+ | 2+ |
| | Non-specific/background staining | No | No | Yes | No |
| Lung cancer (2018-55164F ) | Specific staining intensity | 0 | 1+ | 0 | 0 |
| | Non-specific/background staining | No | No | Yes | No |

4. Staining of Gastric Cancer Tissue Microarrays with Antibody 9

Antibody 9 is selected for staining and analysis of gastric cancer and paracancerous tissue microarray. Antibody 9 is used at a working concentration of 0.2 μg/mL and Abcam EPR19202-244 is used at the recommended working concentration of 0.37 μg/mL to stain 75 cases of gastric cancer and paracancerous tissue microarrays (Shanghai Outdo Biotech Co., Ltd., microarray number: HStm-Ade150CS4-01), respectively. The specific datas are shown in Table 3, and the statistics of staining results are shown in Table 4.

For cancer tissues, the detectable rate of antibody 9 is 60.0% (45/75), with 41.3% (31/75) at ≥2+ staining level; the detectable rate of Abcam EPR19202-244 is 41.3% (31/75), with only 17.3% (13/75) at ≥2+ staining level.

For paracancerous tissues, the detectable rate of antibody 9 is 100% (75/75), with 90.6% (68/75) at ≥2+ staining level; the detection rate of Abcam EPR19202-244 is 98.6% (74/75), with 89.3% (67/75) at ≥2+ staining level.

This shows that antibody 9 is superior to Abcam EPR19202-244 in terms of both specificity and sensitivity.

TABLE 3

Staining of gastric cancer tissue microarrays with Antibody 9

| position of point | Paraffin block number | tissue type | Pathological typing | antibody 9 | Abcam EPR19202-244 |
|---|---|---|---|---|---|
| A1 | D09A0001-B30-C1 | Carcinoma | Adenocarcinoma | 0 | 0 |
| A3 | D09A0007-B30-C1 | Carcinoma | Adenocarcinoma | 0 | 0 |
| A7 | D09A0136-B30-C1 | Carcinoma | Adenocarcinoma | 0 | 0 |
| A11 | D09A0430-B30-C1 | Carcinoma | Adenocarcinoma | 0 | 0 |
| A13 | D09A0477-B30-C1 | Carcinoma | Adenocarcinoma | 0 | 0 |
| A15 | D09A0792-B30-C1 | Carcinoma | Adenocarcinoma | 0 | 0 |
| B1 | D09A0793-B30-C1 | Carcinoma | Adenocarcinoma | 0 | 0 |
| B5 | D09A1314-B30-C1 | Carcinoma | Adenocarcinoma | 0 | 0 |
| B15 | D09A2557-B30-C1 | Carcinoma | Adenocarcinoma | 0 | 0 |
| C3 | D09A2751-B30-C1 | Carcinoma | Adenocarcinoma | 0 | 0 |
| C7 | D09A3150-B30-C1 | Carcinoma | Adenocarcinoma | 0 | 0 |
| D3 | D09A3965-B30-C1 | Carcinoma | Adenocarcinoma | 0 | 0 |
| D7 | D09A4002-B30-C1 | Carcinoma | Adenocarcinoma | 0 | 0 |
| E1 | D09A0352-B30-C1 | Carcinoma | Adenocarcinoma | 0 | 0 |
| E5 | D09A0490-B30-C1 | Carcinoma | Adenocarcinoma | 0 | 0 |
| E11 | D09A1120-B30-C1 | Carcinoma | Adenocarcinoma | 0 | 0 |
| E13 | D09A1352-B30-C1 | Carcinoma | Adenocarcinoma | 0 | 0 |
| F15 | D09A4027-B30-C1 | Carcinoma | Adenocarcinoma | 0 | 0 |
| G5 | D09A2365-B30-C1 | Carcinoma | Adenocarcinoma (Mucinous carcinoma) | 0 | 0 |
| H9 | D09A0397-B30-C1 | Carcinoma | Adenocarcinoma | 0 | 0 |
| H11 | D09A2689-B30-C1 | Carcinoma | Adenocarcinoma | 0 | 0 |
| I11 | D09A0420-B30-C1 | Carcinoma | Adenocarcinoma | 0 | 0 |
| I9 | D09A0341-B30-C1 | Carcinoma | Adenocarcinoma (Mucinous carcinoma, some cancer cells are signet ring-like) | 0 | 0 |
| I5 | D09A0242-B30-C1 | Carcinoma | Adenocarcinoma, partially growing in a mucinous carcinoma way | 0 | 0 |
| C15 | D09A3828-B30-C1 | Carcinoma | Adenocarcinoma, mostly growing in a mucinous carcinoma way | 0 | 0 |
| E9 | D09A1091-B30-C1 | Carcinoma | Adenocarcinoma, partially mucinous adenocarcinoma | 0 | 0 |
| F9 | D09A2345-B30-C1 | Carcinoma | Adenocarcinoma | 0 | 0 |
| F5 | D09A0247-B30-C1 | Carcinoma | Adenocarcinoma, some cancer cells are signet ring-like | 3+ | 2+ |
| G1 | D09A0117-B30-C1 | Carcinoma | Adenocarcinoma, most cancer cells are signet ring-like | 3+ | 3+ |
| H5 | D09A1695-B30-C1 | Carcinoma | Adenocarcinoma, a few cancer cells are signet ring-like | 2+ | 1+ |
| H3 | D09A1328-B30-C1 | Carcinoma | Adenocarcinoma, some cancer cells are signet ring-like | 3+ | 3+ |
| D9 | D09A4024-B30-C1 | Carcinoma | Adenocarcinoma, growing in a mucinous carcinoma way, some cancer | 2+ | 1+ |

TABLE 3-continued

| Staining of gastric cancer tissue microarrays with Antibody 9 | | | | | |
|---|---|---|---|---|---|
| position of point | Paraffin block number | tissue type | Pathological typing | antibody 9 | Abcam EPR19202-244 |
| | | | cells are signet ring-like | | |
| E7 | D09A0613-B30-C1 | Carcinoma | Adenocarcinoma (mostly mucinous carcinoma, some cancer cells are signet ring-like ) | 2+ | 1+ |
| C5 | D09A2972-B30-C1 | Carcinoma | Adenocarcinoma | 3+ | 1+ |
| B3 | D09A1009-B30-C1 | Carcinoma | Adenocarcinoma | 3+ | 2+ |
| A9 | D09A0268-B30-C1 | Carcinoma | Adenocarcinoma | 2+ | 1+ |
| B7 | D09A1516-B30-C1 | Carcinoma | Adenocarcinoma | 2+ | 1 + |
| C9 | D09A3365-B30-C1 | Carcinoma | Adenocarcinoma | 2+ | 1+ |
| C11 | D09A3399-B30-C1 | Carcinoma | Adenocarcinoma | 2+ | 1+ |
| D1 | D09A3912-B30-C1 | Carcinoma | Adenocarcinoma | 2+ | 1+ |
| D11 | D09A4085-B30-P1 | Carcinoma | Adenocarcinoma | 2+ | 1+ |
| D13 | D09A4088-B30-C1 | Carcinoma | Adenocarcinoma | 2+ | 1+ |
| D15 | D09A0267-B30-C1 | Carcinoma | Adenocarcinoma | 1+ | 1+ |
| E15 | D09A1545-B30-C1 | Carcinoma | Adenocarcinoma | 3+ | 2+ |
| F3 | D09A1544-B30-C1 | Carcinoma | Adenocarcinoma | 3+ | 1+ |
| F7 | D09A0664-B30-C1 | Carcinoma | Adenocarcinoma | 3+ | 2+ |
| F11 | D09A3777-B30-C1 | Carcinoma | Adenocarcinoma | 3+ | 2+ |
| F13 | D09A4025-B30-C1 | Carcinoma | Adenocarcinoma | 2+ | 1+ |
| G7 | D09A3436-B30-C1 | Carcinoma | Adenocarcinoma | 2+ | 2+ |
| G11 | D09A3822-B30-C1 | Carcinoma | Adenocarcinoma | 2+ | 2+ |
| H1 | D09A0571-B30-C1 | Carcinoma | Adenocarcinoma | 3+ | 2+ |
| I1 | D09A0107-B30-C1 | Carcinoma | Adenocarcinoma | 1+ | 1+ |
| I13 | D09A0992-B30-C1 | Carcinoma | Adenocarcinoma | 1+ | 1+ |
| I15 | D09A1276-B30-C1 | Carcinoma | Adenocarcinoma | 1+ | 1+ |
| J1 | D09A1421-B30-C1 | Carcinoma | Adenocarcinoma | 2+ | 2+ |
| J3 | D09A3769-B30-C1 | Carcinoma | Adenocarcinoma | 3+ | 2+ |
| I7 | D09A0292-B30-C1 | Carcinoma | Adenocarcinoma | 3+ | 1+ |
| J5 | D09A4015-B30-C1 | Carcinoma | Adenocarcinoma | 2+ | 2+ |
| G3 | D09A2212-B30-C1 | Carcinoma | Adenocarcinoma, partially growing in a mucinous carcinoma way | 1+ | 0 |
| B9 | D09A1781-B30-C1 | Carcinoma | Adenocarcinoma | 1+ | 0 |
| Bl l | D09A1969-B30-C1 | Carcinoma | Adenocarcinoma | 1+ | 0 |
| B13 | D09A2187-B30-C1 | Carcinoma | Adenocarcinoma | 2+ | 0 |
| C1 | D09A2583-B30-C1 | Carcinoma | Adenocarcinoma | 1+ | 0 |
| A5 | D09A0021-B30-C1 | Carcinoma | Adenocarcinoma | 1+ | 0 |
| C13 | D09A3698-B30-P1 | Carcinoma | Adenocarcinoma | 1+ | 0 |
| D5 | D09A3970-B30-C1 | Carcinoma | Adenocarcinoma | 1+ | 0 |
| E3 | D09A0369-B30-C1 | Carcinoma | Adenocarcinoma | 0 | 0 |
| F1 | D09A3833-B30-C1 | Carcinoma | Adenocarcinoma | 2+ | 0 |
| G9 | D09A3441-B30-C1 | Carcinoma | Adenocarcinoma | 1+ | 0 |
| G13 | D09A0121-B30-C1 | Carcinoma | Adenocarcinoma | 1+ | 0 |
| H7 | D09A3181-B30-C1 | Carcinoma | Adenocarcinoma | 2+ | 0 |
| H13 | D09A0552-B30-C1 | Carcinoma | Adenocarcinoma | 0 | 0 |
| H15 | D09A0410-B30-C1 | Carcinoma | Adenocarcinoma | 1+ | 0 |
| G15 | D09A0471-B30-C1 | Carcinoma | Adenocarcinoma, most cancer cells are signet ring-like | 1+ | 0 |
| I3 | D09A0137-B30-Cl | Carcinoma | Signet-ring cell carcinoma | 0 | 0 |
| A6 | D09A0021-B30-P1 | Paracancer-ous | Fundic gland mucosa | 3+ | 3+ |
| A8 | D09A0136-B30-P1 | Paracancer-ous | Fundic gland mucosa | 2+ | 3+ |
| A2 | D09A0001-B30-P1 | Paracancer-ous | Fundic gland mucosa | 3+ | 3+ |
| A12 | D09A0430-B30-P1 | Paracancer-ous | Fundic gland mucosa | 3+ | 2+ |
| A14 | D09A0477-B30-P1 | Paracancer-ous | Fundic gland mucosa | 1+ | 1+ |
| B2 | D09A0793-B30-P1 | Paracancer-ous | Fundic gland mucosa | 2+ | 2+ |
| B4 | D09A1009-B30-P1 | Paracancer-ous | Fundic gland mucosa | 3+ | 3+ |
| B6 | D09A1314-B30-P1 | Paracancer-ous | Fundic gland mucosa | 2+ | 2+ |

TABLE 3-continued

| Staining of gastric cancer tissue microarrays with Antibody 9 | | | | | |
|---|---|---|---|---|---|
| position of point | Paraffin block number | tissue type | Pathological typing | antibody 9 | Abcam EPR19202-244 |
| B12 | D09A1969-B30-P1 | Paracancer-ous | Fundic gland mucosa | 3+ | 2+ |
| B14 | D09A2187-B30-P1 | Paracancer-ous | Fundic gland mucosa | 3+ | 2+ |
| C4 | D09A2751-B30-P1 | Paracancer-ous | Fundic gland mucosa | 3+ | 2+ |
| C8 | D09A3150-B30-P1 | Paracancer-ous | Fundic gland mucosa | 3+ | 3+ |
| C10 | D09A3365-B30-P1 | Paracancer-ous | Fundic gland mucosa | 2+ | 3+ |
| C14 | D09A3698-B30-C1 | Paracancer-ous | Fundic gland mucosa | 3+ | 3+ |
| D2 | D09A3912-B30-P1 | Paracancer-ous | Fundic gland mucosa | 3+ | 2+ |
| D4 | D09A3965-B30-P1 | Paracancer-ous | Fundic gland mucosa | 3+ | 3+ |
| D6 | D09A3970-B30-P1 | Paracancer-ous | Fundic gland mucosa | 3+ | 3+ |
| D8 | D09A4002-B30-P1 | Paracancer-ous | Fundic gland mucosa | 3+ | 2+ |
| D14 | D09A4088-B30-P1 | Paracancer-ous | Fundic gland mucosa | 3+ | 3+ |
| D16 | D09A0267-B30-P1 | Paracancer-ous | Fundic gland mucosa | 2+ | 2+ |
| E4 | D09A0369-B30-P1 | Paracancer-ous | Fundic gland mucosa | 2+ | 2+ |
| E6 | D09A0490-B30-P1 | Paracancer-ous | Fundic gland mucosa | 2+ | 1+ |
| E8 | D09A0613-B30-P1 | Paracancer-ous | Fundic gland mucosa | 3+ | 3+ |
| E10 | D09A1091-B30-P1 | Paracancer-ous | Fundic gland mucosa | 3+ | 2+ |
| E14 | D09A1352-B30-P1 | Paracancer-ous | Fundic gland mucosa | 2+ | 2+ |
| E16 | D09A1545-B30-P1 | Paracancer-ous | Fundic gland mucosa | 2+ | 2+ |
| F4 | D09A1544-B30-P1 | Paracancer-ous | Fundic gland mucosa | 3+ | 2+ |
| F6 | D09A0247-B30-P1 | Paracancer-ous | Fundic gland mucosa | 2+ | 1+ |
| F8 | D09A0664-B30-P1 | Paracancer-ous | Fundic gland mucosa | 3+ | 2+ |
| F10 | D09A2345-B30-P1 | Paracancer-ous | Fundic gland mucosa | 3+ | 2+ |
| Fl 4 | D09A4025-B30-P1 | Paracancer-ous | Fundic gland mucosa | 1+ | 1+ |
| F16 | D09A4027-B30-P1 | Paracancer-ous | Fundic gland mucosa | 2+ | 2+ |
| G4 | D09A2212-B30-P1 | Paracancer-ous | Fundic gland mucosa | 3+ | 2+ |
| G6 | D09A2365-B30-P1 | Paracancer-ous | Fundic gland mucosa | 3+ | 2+ |
| G8 | D09A3436-B30-P1 | Paracancer-ous | Fundic gland mucosa | 3+ | 3+ |
| G10 | D09A3441-B30-P1 | Paracancer-ous | Fundic gland mucosa | 3+ | 2+ |
| G12 | D09A3822-B30-P1 | Paracancer-ous | Fundic gland mucosa | 2+ | 2+ |
| G14 | D09A0121-B30-P1 | Paracancer-ous | Fundic gland mucosa | 2+ | 2+ |
| H2 | D09A0571-B30-P1 | Paracancer-ous | Fundic gland mucosa | 3+ | 2+ |
| D12 | D09A4085-B30-C1 | Paracancer-ous | Fundic gland mucosa | 3+ | 3+ |
| H4 | D09A1328-B30-P1 | Paracancer-ous | Fundic gland mucosa | 3+ | 2+ |
| H6 | D09A1695-B30-P1 | Paracancer-ous | Fundic gland mucosa | 3+ | 3+ |
| H8 | D09A3181-B30-P1 | Paracancer-ous | Fundic gland mucosa | 3+ | 2+ |
| H10 | D09A0397-B30-P1 | Paracancer-ous | Fundic gland mucosa | 2+ | 2+ |
| H12 | D09A2689-B30-P1 | Paracancer-ous | Fundic gland mucosa | 3+ | 3+ |

TABLE 3-continued

Staining of gastric cancer tissue microarrays with Antibody 9

| position of point | Paraffin block number | tissue type | Pathological typing | antibody 9 | Abcam EPR19202-244 |
|---|---|---|---|---|---|
| J2 | D09A1421-B30-P1 | Paracancer-ous | Fundic gland mucosa | 2+ | 2+ |
| H16 | D09A0410-B30-P1 | Paracancer-ous | Fundic gland mucosa | 3+ | 2+ |
| I2 | D09A0107-B30-P1 | Paracancer-ous | Fundic gland mucosa | 3+ | 3+ |
| I6 | D09A0242-B30-P1 | Paracancer-ous | Fundic gland mucosa | 2+ | 2+ |
| I14 | D09A0992-B30-P1 | Paracancer-ous | Fundic gland mucosa | 3+ | 3+ |
| I16 | D09A1276-B30-P1 | Paracancer-ous | Fundic gland mucosa | 3+ | 3+ |
| A16 | D09A0792-B30-P1 | Paracancer-ous | Fundic gland mucosa, with intestinal metaplasia | 2+ | 2+ |
| A10 | D09A0268-B30-P1 | Paracancer-ous | Fundic gland mucosa, with intestinal metaplasia | 2+ | 2+ |
| B16 | D09A2557-B30-P1 | Paracancer-ous | Fundic gland mucosa, with intestinal metaplasia (small-intestinal metaplasia) | 2+ | 2+ |
| C2 | D09A2583-B30-P1 | Paracancer-ous | Fundic gland mucosa, with small-intestinal metaplasia | 3+ | 2+ |
| C6 | D09A2972-B30-P1 | Paracancer-ous | Fundic gland mucosa, with intestinal metaplasia | 2+ | 2+ |
| C12 | D09A3399-B30-P1 | Paracancer-ous | Fundic gland mucosa, with intestinal metaplasia | 3+ | 2+ |
| D10 | D09A4024-B30-P1 | Paracancer-ous | Fundic gland mucosa, with intestinal metaplasia | 2+ | 2+ |
| F12 | D09A3777-B30-P1 | Paracancer-ous | Fundic gland mucosa, with intestinal metaplasia | 3+ | 2+ |
| H14 | D09A0552-B30-P1 | Paracancer-ous | Fundic gland mucosa, with intestinal metaplasia | 1+ | 1+ |
| E12 | D09A1120-B30-P1 | Paracancer-ous | Fundic gland mucosa and pyloric gland, with intestinal metaplasia | 2+ | 2+ |
| A4 | D09A0007-B30-P1 | Paracancer-ous | pyloric gland mucosa, with intestinal metaplasia | 2+ | 2+ |
| B8 | D09A1516-B30-P1 | Paracancer-ous | pyloric gland mucosa, with intestinal metaplasia | 2+ | 2+ |
| B10 | D09A1781-B30-P1 | Paracancer-ous | pyloric gland mucosa, with intestinal metaplasia | 2+ | 2+ |
| J6 | D09A4015-B30-P1 | Paracancer-ous | pyloric gland mucosa, with intestinal metaplasia | 1+ | 1+ |
| E2 | D09A0352-B30-P1 | Paracancer-ous | pyloric gland mucosa, with intestinal metaplasia | 1+ | 0 |

TABLE 3-continued

Staining of gastric cancer tissue microarrays with Antibody 9

| position of point | Paraffin block number | tissue type | Pathological typing | antibody 9 | Abcam EPR19202-244 |
| --- | --- | --- | --- | --- | --- |
| I12 | D09A0420-B30-P1 | Paracancer-ous | pyloric gland mucosa, with intestinal metaplasia | 2+ | 2+ |
| J4 | D09A3769-B30-P1 | Paracancer-ous | pyloric gland mucosa, with intestinal metaplasia | 2+ | 2+ |
| I4 | D09A0137-B30-P1 | Paracancer-ous | pyloric gland mucosa, with intestinal metaplasia | 2+ | 2+ |
| I10 | D09A0341-B30-P1 | Paracancer-ous | pyloric gland mucosa, with intestinal metaplasia | 1+ | 1+ |
| C16 | D09A3828-B30-P1 | Paracancer-ous | pyloric gland mucosa | 2+ | 2+ |
| F2 | D09A3833-B30-P1 | Paracancer-ous | pyloric gland mucosa | 3+ | 2+ |
| G2 | D09A0117-B30-P1 | Paracancer-ous | pyloric gland mucosa | 2+ | 2+ |
| G16 | D09A0471-B30-P1 | Paracancer-ous | pyloric gland mucosa | 2+ | 2+ |
| I8 | D09A0292-B30-P1 | Paracancer-ous | pyloric gland mucosa | 1+ | 2+ |

TABLE 4

Statistics of staining results of gastric cancer tissue microarrays with Claudin18.2 diagnostic antibody

| Tissue type | Staining intensity | Antibody 9 | Abcam EPR19202-244 |
| --- | --- | --- | --- |
| Cancer tissue | 0 | 30 | 44 |
| | 1+ | 15 | 18 |
| | 2+ | 19 | 11 |
| | 3+ | 11 | 2 |
| Paracancerous tissue | 0 | 0 | 1 |
| | 1+ | 7 | 7 |
| | 2+ | 31 | 49 |
| | 3+ | 37 | 18 |
| Total | | 150 | 150 |

Example 4. Epitope Analysis

ELISA method: By detecting the binding of antibody 7 and antibody 9 to different peptides of the antigen, the epitopes of antibody binding are analyzed.

Based on the sequence of the immunogen (Claudin18.2 C-terminal peptide), it is divided into 21 peptides according to the principle of 15aa length and 12aa overlap, and the corresponding peptides are chemically synthesized and modified with biotin at the N-terminal. Each peptide is captured with Neutravidin plate (CAT: 15128 Invitrogen) and then incubated with 10 μg/mL of Claudin18.2 antibody (antibody 7 and antibody 9). HRP-labeled goat anti-mouse (CAT: A0168 SIGMA) is used as secondary antibody, and developed using a substrate chromogenic solution for 5 minutes, followed by the addition of 2M $H_2SO_4$ to terminate the chromogenic development, and the binding of the antibodies and each of the peptides is characterized by measuring the absorbance at OD450 nm.

Figure 6:
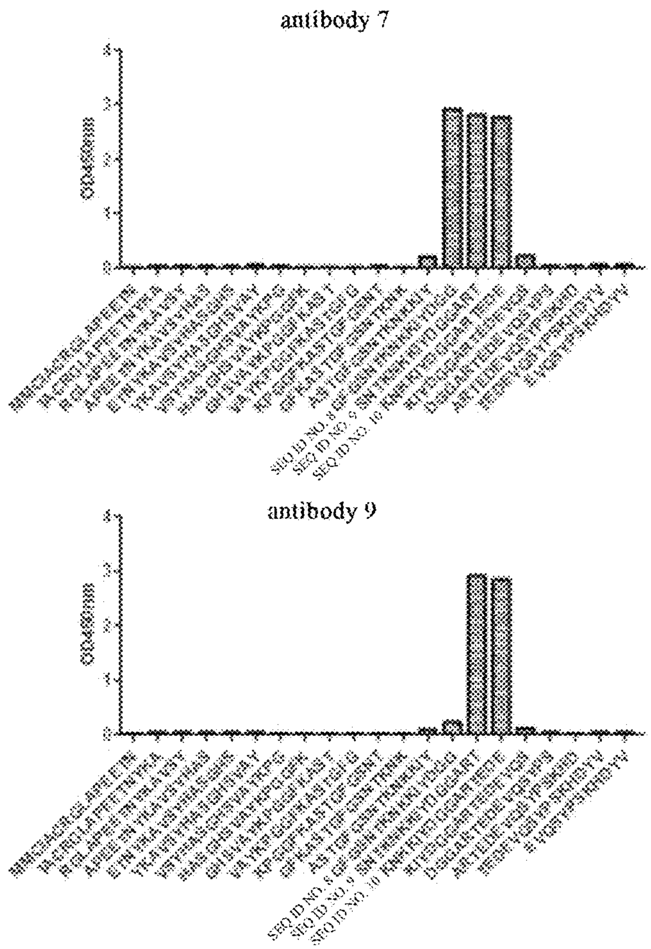
FIG. 6: Showing the results of ELISA analysis of epitopes. The twenty one amino acid sequences on the x-axis, from left to right, are as follows: positions 1-15 of SEQ ID NO: 3, positions 4-18 of SEQ ID NO: 3, positions 7-21 of SEQ ID NO: 3, positions 10-24 of SEQ ID NO: 3, positions 13-27 of SEQ ID NO: 3, positions 16-30 of SEQ ID NO: 3, positions 19-33 of SEQ ID NO: 3, positions 22-36 of SEQ ID NO: 3, positions 25-39 of SEQ ID NO: 3, positions 28-42 of SEQ ID NO: 3, positions 31-45 of SEQ ID NO: 3, positions 34-48 of SEQ ID NO: 3, positions 37-51 of SEQ ID NO: 3, SEQ ID NO: 8, SEQ ID NO: 9, SEQ ID NO: 10, positions 49-63 of SEQ ID NO: 3, positions 52-66 of SEQ ID NO: 3, positions 55-69 of SEQ ID NO: 3, positions 57-71 of SEQ ID NO: 3, and positions 60-71 of SEQ ID NO: 3.

The ELISA results are shown in FIG. 6. The binding peptide sequence characteristics of antibody 9 is shown in SEQ ID NO: 6: KNKKIYDGGART; the binding peptide sequence characteristics of antibody 7 is shown in SEQ ID NO: 7: KNKKIYDGG.

All documents mentioned herein are incorporated by reference in this application as if each document were individually incorporated by reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. An antibody or antigen-binding fragment thereof, wherein the antibody is an antibody produced by the hybridoma cell line deposited with the accession number CCTCCNO.C202007 or CCTCCNO.C202008, wherein the antibody produced by the hybridoma cell line CCTCCNO.C202007 is antibody 9 and the antibody produced by the hybridoma cell line CCTCCNO.C202008 is antibody 7.

2. The antibody or antigen-binding fragment thereof according to claim 1, wherein, the antibody or antigen-binding fragment is capable of recognizing an antigenic peptide comprising the sequence shown in SEQ ID NO: 7 (KNKKIYDGG).

3. The antibody or antigen-binding fragment thereof according to claim 2, the antibody or antigen-binding fragment is capable of recognizing a peptide comprising the sequence shown in SEQ ID NO: 6 (KNKKIYDGGART).

4. The antibody or antigen-binding fragment thereof according to claim 1, wherein the antibody or antigen-binding fragment is capable of recognizing an antigenic peptide comprising the sequence shown in SEQ ID NO: 8 (GFGSNTKNKKIYDGG), 9 (SNTKNKKIYDGGART) or 10 (KNKKIYDGGARTEDE).

5. The antibody or antigen binding fragment thereof according to claim 1, wherein the antibody fragment is a scFv, a Fab fragment, a Fv fragment, or a F(ab')2 fragment.

6. A conjugate, comprising the antibody or antigen-binding fragment thereof according to claim 1, and at least one detectable label.

7. The conjugate according to claim 6, wherein, the at least one detectable label is a fluorescent label, a chromogenic label, a luminescent label, a chromophore label, a radioisotope label, an isotope label, an isobaric label, an enzyme label, a particle label, a nucleic acid or a protein.

8. An assay kit comprising the antibody or antigen-binding fragment thereof according to claim 1.

9. A hybridoma, wherein the deposit accession number of the hybridoma is CCTCCNO.C202007 or CCTCCNO.C202008.

10. A method for detecting the expression of Claudin18.2 in a sample to be tested, wherein the method comprises: contacting the sample to be tested with the antibody or antigen-binding fragment thereof according to claim 1; detecting the state of a complex formed by the antibody or antigen-binding fragment and Claudin18.2.

11. The method according to claim 10, wherein the Claudin 18.2 comprises the amino acid sequence of SEQ ID NO: 2.

12. A method for analyzing Claudin18.2 in a tumor, wherein the method comprises:

(i) contacting a sample comprising a tumor cell with the antibody or antigen binding fragment thereof according to claim 1;

(ii) detecting the amount of a complex formed by the antibody or antigen-binding fragment, and Claudin 18.2.

13. The method according to claim 12, wherein the tumor cell is a gastric cancer cell, an esophageal cancer cell, a pancreatic cancer cell, a lung cancer cell, an ovarian cancer cell, a colon cancer cell, a liver cancer cell, a head and neck cancer cell, or a biliary system tumor cell.

* * * * *